US010634756B2

(12) United States Patent
Zuccolotto et al.

(10) Patent No.: US 10,634,756 B2
(45) Date of Patent: *Apr. 28, 2020

(54) MRI PHANTOM INCLUDING HOLLOW FLUID FILLED TUBULAR TEXTILES FOR CALIBRATED ANISOTROPIC IMAGING

(71) Applicants: Psychology Software Tools, Inc., Sharpsburg, PA (US); University of Pittsburgh—Of the Commonwealth System of Higher Education, Pittsburgh, PA (US)

(72) Inventors: Anthony P Zuccolotto, Freeport, PA (US); Leroy K Basler, Irwin, PA (US); John Dzikiy, Pittsburgh, PA (US); Walter Schneider, Pittsburgh, PA (US); Richard A Shaffer, Apollo, PA (US)

(73) Assignees: PSYCHOLOGY SOFTWARE TOOLS, INC., Sharpsburg, PA (US); UNIVERSITY OF PITTSBURGH--OF THE COMMONW, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/504,912

(22) Filed: Jul. 8, 2019

(65) Prior Publication Data
US 2019/0331751 A1    Oct. 31, 2019

Related U.S. Application Data

(63) Continuation of application No. 15/403,304, filed on Jan. 11, 2017, now Pat. No. 10,345,415, which is a
(Continued)

(51) Int. Cl.
*G01R 33/58*     (2006.01)
*A61B 5/055*     (2006.01)
(Continued)

(52) U.S. Cl.
CPC .............. *G01R 33/58* (2013.01); *A61B 5/055* (2013.01); *G01R 33/31* (2013.01);
(Continued)

(58) Field of Classification Search
CPC .. G01R 33/58; G01R 33/31; G01R 33/56341; A61B 5/055; G09B 23/28
See application file for complete search history.

(56) References Cited

U.S. PATENT DOCUMENTS 6,409,515 B1    6/2002    Persohn et al.
6,720,766 B2    4/2004    Parker et al.
(Continued)

FOREIGN PATENT DOCUMENTS

WO    2012125829    9/2012
WO    2016007939    1/2016

OTHER PUBLICATIONS

Farrher et al., Novel multisection design of anisotropic diffusion phantoms, Magnetic Resonance Imaging 30, pp. 518-526, 2012 (Year: 2012).*
(Continued)

*Primary Examiner* — Daniel R Miller
(74) *Attorney, Agent, or Firm* — Blynn L. Shideler; Krisanne Shideler; BLK Law Group

(57) ABSTRACT

A universal, modular, temperature controlled MRI phantom for calibration and validation for anisotropic and isotropic imaging comprises an outer insulating shell configured to be received within an MRI chamber; an inner shell received within the outer insulating shell; a fluid conduits adjacent the inner shell for receiving temperature controlling fluid or gas cycling there-through; and a series of stacked layers of frames containing test points for the MRI phantom, each layer including at least one fiducial and including at least some anisotropic imaging test points in at least one frame
(Continued)

and at least one isotropic imaging test point in at least one frame. The anisotropic imaging comprises hollow tubular textile fibers, wherein each hollow tubular fiber has an outer diameter of less than 50 microns and an inner diameter of less than 20 microns, wherein at least some hollow tubular fibers are filled with a fluid.

11 Claims, 19 Drawing Sheets

Related U.S. Application Data continuation of application No. PCT/US2015/040075, filed on Jul. 11, 2015.

(60) Provisional application No. 62/023,338, filed on Jul. 11, 2014.

(51) Int. Cl.
  *G09B 23/28* (2006.01)
  *G01R 33/31* (2006.01)
  *G01R 33/563* (2006.01)
  *A61B 5/00* (2006.01)

(52) U.S. Cl.
  CPC ....... *G01R 33/56341* (2013.01); *G09B 23/28* (2013.01); *A61B 5/0042* (2013.01)

(56) References Cited

U.S. PATENT DOCUMENTS

| | | | |
|---|---|---|---|
| 6,744,039 B1 | 6/2004 | DiFilippo | |
| 7,521,931 B2 | 4/2009 | Ogrezeanu et al. | |
| 7,529,397 B2 | 5/2009 | Wang et al. | |
| 7,667,458 B2 | 2/2010 | Yoo et al. | |
| 8,076,937 B2 | 12/2011 | Holthuizen et al. | |
| 8,134,363 B2 | 3/2012 | Yanasak et al. | |
| 8,593,142 B2 | 11/2013 | Mori et al. | |
| 8,643,369 B2 | 2/2014 | Krzyzak | |
| 2006/0165308 A1 | 7/2006 | Chakraborty | |
| 2006/0195030 A1 | 8/2006 | Ogrezeanu | |
| 2007/0124117 A1 | 5/2007 | Zhang | |
| 2007/0223799 A1 | 9/2007 | Weiss | |
| 2010/0167251 A1 | 7/2010 | Boutchko | |
| 2012/0068699 A1 | 3/2012 | Horkay | |
| 2013/0279772 A1 | 10/2013 | Stedele | |
| 2017/0184696 A1 | 6/2017 | Zuccolotto et al. | |

OTHER PUBLICATIONS

Johansen-Berg et al. Diffusion MRI, From Quantitative Measurement to In-vivo Neuroanatomy, Elsevier, 2nd ed., 2014, pp. 459-460 (Year: 2014).*

Poupon, New Diffusion Phantoms Dedicated to the Study and Validation of High-Angular-Resolution Diffusion Imaging (HARDI) Models, Magnetic Resonance in Medicine 60:1276-1283, 2008.

Reischauer et al., Construction of a Temperature-Controlled Diffusion Phantom for Quality Control of Diffusion Measurements, Journal of Magnetic Resonance Imaging 29:692-698,2009.

Zhou et al., Coaxially Electrospun Axon-Mimicking Fibers for Diffusion Magnetic Resonance Imaging, ACS Appl. Mater. Interfaces 2012, 4, 6311-6316.

Juneja, Novel Phantoms and Post-Processing for Diffusion Spectrum Imaging, Dissertation, 2012, available at https://digitalcommons.library. tmc.edu/cg ilviewcontent.cgi?article= 1291 &context= utgsbs dissertations.

Teeuw, Methods for validating the anatomical trajectory of reconstructed fibre tracts in diffusion magnetic resonance fibre tractography, Master thesis, Utrecht University, Netherlands, Oct. 2013.

* cited by examiner

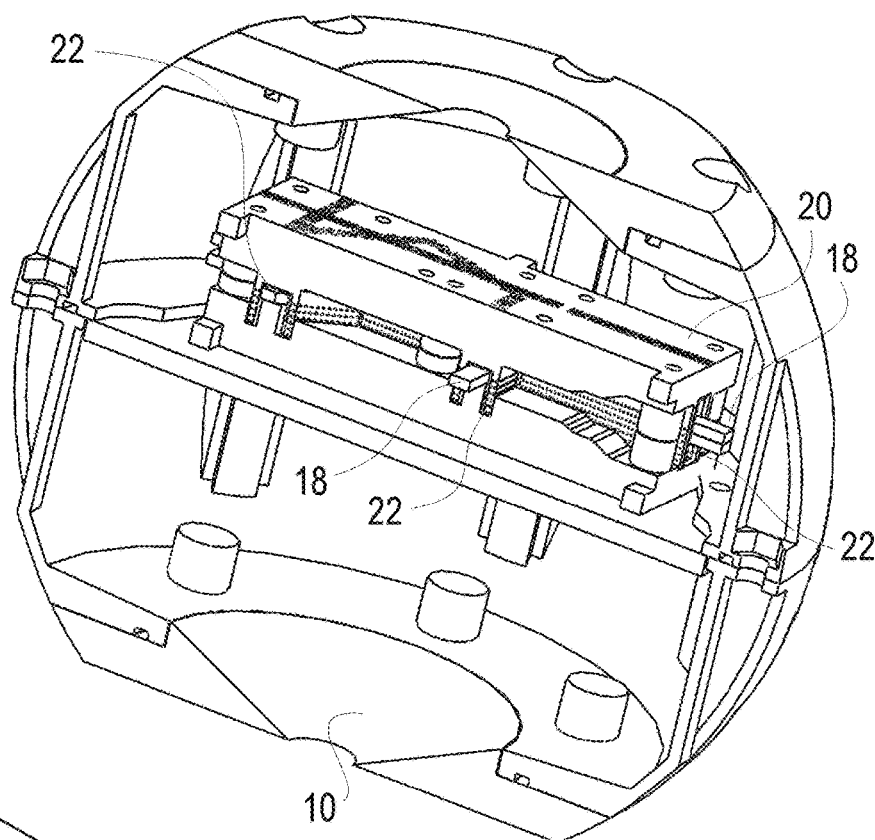
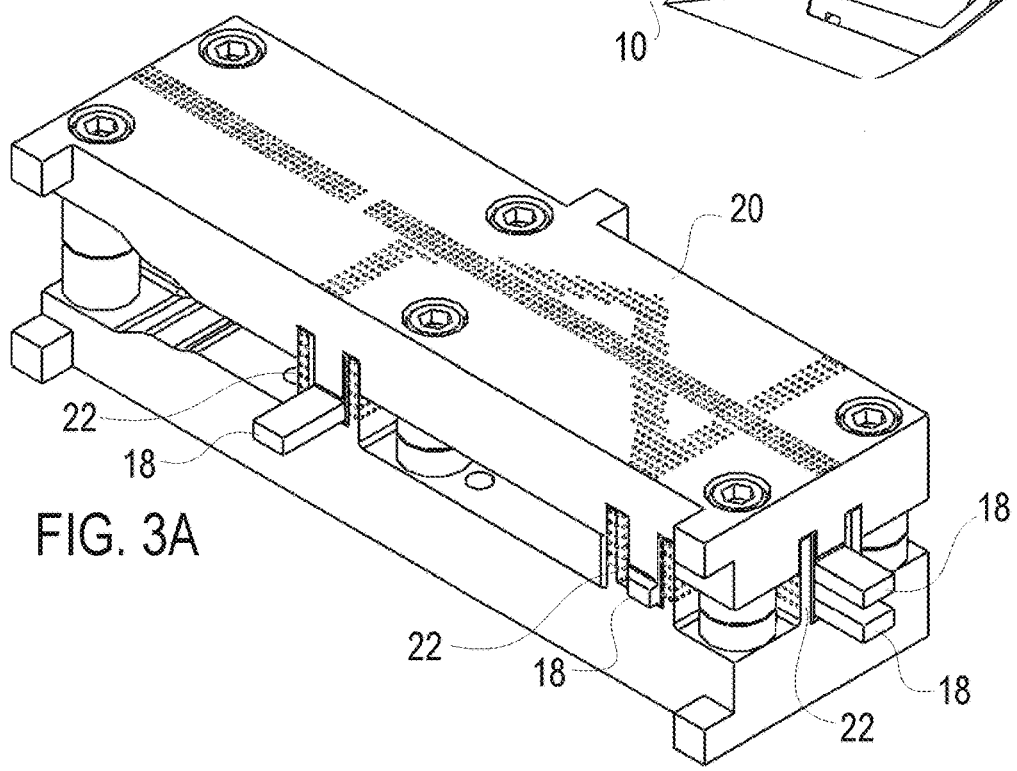

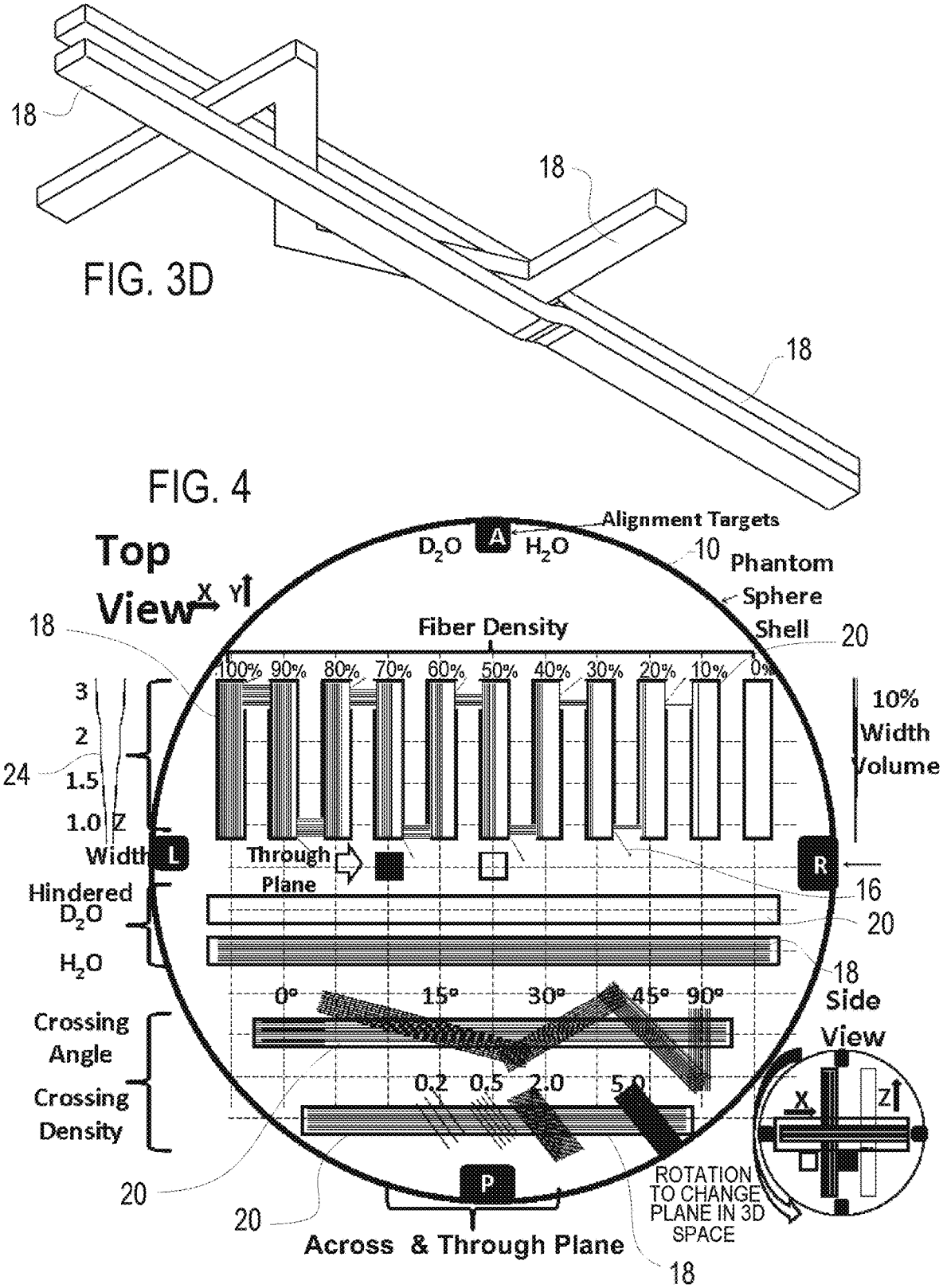

MRI T1 STRUCTURAL IMAGE

FIBERS AIR FILLED    FIBERS WATER FILLED

MRI Diffusion Image

FIBERS AIR FILLED    FIBERS WATER FILLED

CROSSING FRAME LAYER

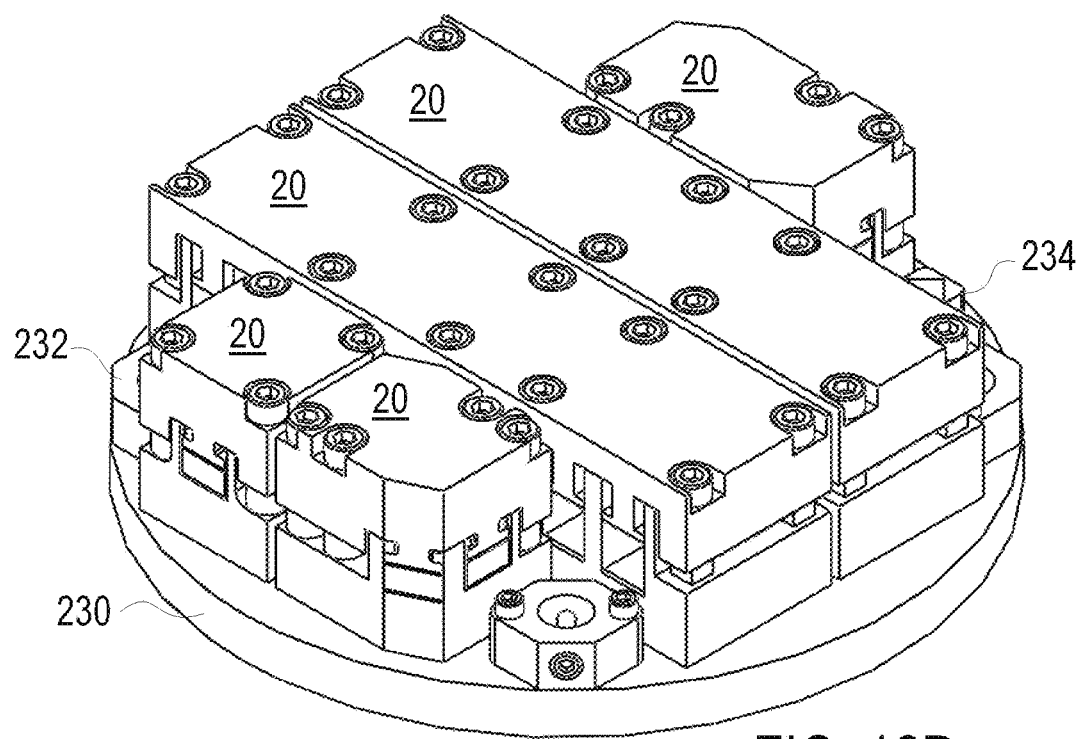
FIG. 12D
FIG. 13
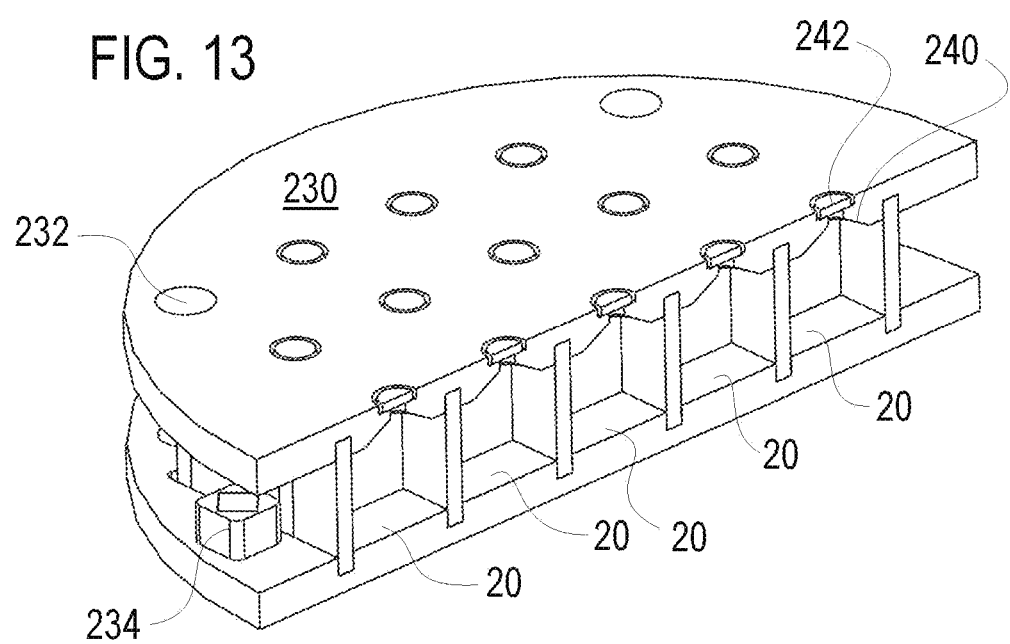

MRI PHANTOM INCLUDING HOLLOW FLUID FILLED TUBULAR TEXTILES FOR CALIBRATED ANISOTROPIC IMAGING

RELATED APPLICATIONS

This application is a continuation of U.S. patent application Ser. No. 15/403,304 filed Jan. 11, 2017 and titled "Universal, Modular Temperature Controlled MRI Phantom for Calibrated Anisotropic and Isotropic Imaging including Hollow Fluid Filled Tubular Textiles for Calibrated Anisotropic Imaging" and which published Jun. 29, 2017 as publication number 2017-0184696 and issued Jul. 9, 2019 as U.S. Pat. No. 10,345,415, which publication is incorporated herein by reference.

U.S. patent application Ser. No. 15/403,304 is a continuation of International Application No PCT/US2015/040075 filed on Jul. 11, 2015 and titled "Universal, Modular Temperature Controlled MRI Phantom for Calibrated Anisotropic and Isotropic Imaging including Hollow Fluid Filled Tubular Textiles for Calibrated Anisotropic Imaging" and which published Jan. 14, 2016 as Publication WO 2016/007939, which publication is incorporated herein by reference.

International Application No PCT/US2015/040075 claims priority to U.S. Patent Application Ser. No. 62/023,338 filed Jul. 11, 2014, titled "Hollow Fluid Filled Tubular Textile-based MRI Phantom for Calibrated Anisotropic Imaging" which application is incorporated herein by reference in its entirety.

BACKGROUND INFORMATION

1. Field of the Invention

The present invention relates to a universal, modular, temperature controlled MRI phantom for calibration and validation for anisotropic and isotropic imaging which may include hollow fluid filled tubular textile-based MRI phantom for calibrated anisotropic imaging.

2. Background Information

This patent describes a technology innovation that could provide better calibration of brain imaging for brain trauma that impacts an estimated 4 million US citizens annually an estimated 300,000 veterans from recent military conflicts that have had brain trauma and potentially traumatic brain injury (TBI).

MRI

Since inception in the 70's, Magnetic Resonance Imaging (MRI) has allowed research and diagnostic imaging of humans and animals. MRI involves using a combination of high strength magnetic fields and brief radio frequency pulses to image tissue, typically by imaging the dipole movement/spin of hydrogen protons. MRI has long provided two and three dimensional imaging of internal tissue, tissue structure, and can provide imaging of functioning processes of tissue called "Functional MRI" or fMRI.

Diffusion MRI (or dMRI) is an MRI method or technology which allows the mapping of the diffusion process of molecules, mainly water, in biological tissue non-invasively. Since the earliest developments in the 80s, diffusion MRI, also referred to as diffusion tensor imaging or DTI, has seen extraordinary advancement. Diffusion tensor imaging (DTI) is important when a tissue—such as the neural axons of white matter in the brain or muscle fibers in the heart—has an internal fibrous structure analogous to the anisotropy of some crystals. Water will then diffuse more rapidly in the direction aligned with the internal structure, and more slowly as it moves perpendicular to the preferred direction. This is a well developed area of MRI research with several text books on these points, such as Johansen-Berg H. Behrens T. E. J., Diffusion MRI: From quantitative measurement to in-vivo neuroanatomy London Elsevier, 2009, and Jones D. K., Diffusion MRI: Theory, Methods, and Applications, New York: Oxford University Press, 2010.

The advanced work in MRI is also permitting highly detailed neural pathway mapping, sometimes known tractography or fiber tracking. Tractography or fiber tracking is a 3D MRI modeling technique used to visually represent neural tracts (or other biologic tracts) using data collected by DTI. Recent textbooks applying the methods to map white matter pathways include Oishi K., F. A. V., van Zijl P. C. M., Mori S., *MRI Atlas of Human White Matter*, Amsterdam: Elsevier, 2010 and Catani M, Thiebaut de Schotten, M, Atlas of Human Brain Connections, New York: Oxford University Press, 2013.

One MRI technology is known as high definition fiber tracking, or HDFT, and is used to provide extremely highly detailed images of the brain's fiber network accurately reflecting brain anatomy observed in surgical and laboratory studies, as discussed in a report from the University of Pittsburgh, School of Medicine in the August, 2012 issue of Neurosurgery. The findings of this report show that HDFT MRI scans can provide valuable insight into patient symptoms and the prospect for recovery from brain injuries, and can help surgeons plan their approaches to remove tumors and abnormal blood vessels in the brain. One author Juan Fernandez-Miranda, M. D., assistant professor, Department of Neurological Surgery, Pitt School of Medicine, noted that "in deep brain surgery, the neurosurgeon may need to cut or push brain fiber tracts, meaning the neuronal cables connecting the critical brain areas, in order to get to a mass." adding that "HDFT is an (MRI) imaging tool that can show us these fiber tracts so that we can make informed choices when we plan surgery." Co-author of this report and co-inventor of the present invention, Walter Schneider, Ph.D., professor, Learning and Research Development Center (LRDC), Department of Psychology, University of Pittsburgh, who led the team that developed HDFT has elaborated that "a sophisticated MR scanner is used to obtain data for HDFT images, which are based on the diffusion of water through brain cells that transmit nerve impulses. Like a cable of wires, each tract is composed of many fibers and contains millions of neuronal connections. Other MR-based fiber tracking techniques, such as diffusion tensor imaging, cannot accurately follow a set of fibers when they cross another set, nor can they reveal the endpoints of the tract on the surface of the brain." The instant application references the work discussed at the Schneider Laboratory at the LRDC (*http://www.lidc.pitt.edu/schneiderlab/*) for further background on the advancement, current status, and potential of anisotropic imaging and fiber tracking techniques with advanced MRI technologies, which work forms the background for the present invention.

Using advanced, non-invasive, in vivo diffusion imaging techniques combined with HDFT analysis and visualization, the Schneider Laboratory advances clinical research in the diagnosis and treatment of neurological pathology and trauma. The Schneider Laboratory works with the Neurological Surgery Department at UPMC to visualize fiber tracts within the brain in three dimensions in order to plan the most effective and least damaging pathways of tumor excision in patients suffering from various forms of brain cancer. Additionally, the Schneider Laboratory has been engaged in a Department of Defense and Veterans Administration funded HDFT projects to localize the fiber breaks caused by traumatic brain injuries (TBI), which cannot reliably be seen with the then current standard computed axial tomography (CAT or CT) scans or then available MRI scans in mild traumatic brain injury (mTBI), aiding the diagnosis and prognosis of patient brain trauma.

Others have developed fiber tracking technologies using MRI based scans. Consider, the S. Mark Taper Foundation Imaging Center at Cedars-Sinai which offers diffusion tensor imaging (DTI) fiber tracking and functional (fMRI) motor mapping using magnetic resonance imaging fused with 3D anatomical image of a brain to aid in surgical planning.

U.S. Pat. Publication No. 2006-0269107, now U.S. Pat. No. 7,529,397 developed by Siemens Medical Solutions USA, Inc. discloses methods for automatically generating regions of fiber tracking seeding points in diffusion tensor images.

The Johns Hopkins University's U.S. Pat. No. 8,593,142 discloses a system and associated method of automated fiber tracking of human brain white matter using diffusion tensor imaging.

U.S. Pat. Publication No. 2006-0165308 discloses a neighborhood relevance component that considers diffusion tensor matrices from neighboring pixels or voxels.

U.S. Pat. No. 8,076,937, developed by Koninklijke Philips Electronics N.V. of Eindhoven, N L, discloses diffusion data processing apparatus comprising a "segmenter" arranged to segment the diffusion tensor data according to at least one segmentation model representing at least part of a fiber bundle.

U.S. Pat. Publication No. 2007-0124117 discloses a system determining a direction of tracking a fiber based on a vector corresponding to a largest value of a set of values for a tensor.

U.S. Pat. Publication No. 2013-0279772, developed by BrainLAB A G of Feldkirchen, Germany (BrainLAB), discloses a method for finding fibers in image data of a brain which matches a functional atlas of the brain to an image data set which represents a medical image of the brain; performs functional atlas segmentation in order to segment the image data set into functional areas; and uses the segmented image data set to determine at least one seed point for a fiber tracking algorithm; and performing fiber tracking in order to find the fiber.

MRI Phantoms

As advanced MRI systems and technologies are developed, tested and/or placed in operation, the accuracy of the technology must be verified or validated. Validation may be defined as process wherein the accuracy of the technology/imaging algorithms is proven or verified. Further, the accuracy of the associated system must also be periodically verified (i.e., MRI system calibrated—also referenced as Quality Control aspects) to ensure original and ongoing accurate results and safe operation of the MRI systems. Generally speaking, calibration and/or test measurements for an MRI system are performed using an imaging phantom or more commonly referenced as a phantom. A phantom is any structure that contains one or more known tissue substitutes, or known MRI signal substances, forming one or typically more test points, and often is used to simulate the human body. A tissue substitute is defined as any material that simulates a body of tissue. Thus a phantom may be defined as a specially designed object that is scanned or imaged in the field of medical imaging to evaluate, analyze, and tune the performance of various imaging devices. A phantom is more readily available and provides more consistent results than the use of a living subject or cadaver, and likewise avoids subjecting a living subject to direct risk.

Numerous phantoms have been developed for various imaging techniques. For example, U.S. Pat. No. 6,744,039 relates to a fillable phantom which includes a container, a porous medium within the container, and a connector for filling the container with a radioactive solution.

U.S. Pat. No. 6,720,766 relates to a thin film phantom for testing and measuring the performance of magnetic resonance imaging (MRI) and x-ray computed tomography (CT) imaging systems. The phantom includes a planar medium and a plurality of individually sub-resolvable scatters having preselected magnetic resonance properties within a pattern of resolvable regions on the surface of the medium.

U.S. Pat. No. 6,409,515 describes a phantom which includes a plurality of segments having unique identifiers, the segments joining together to form a polyhedron around an inner plate.

Electronics and Telecommunications Research Institute's U.S. Pat. No. 7,667,458 discloses a phantom for Diffusion Tensor Imaging (DTI) to measure the main physical quantities of diffusion tensors, such as diffusion anisotrophy, a diffusion principal axis and a route of the diffusion principal axis, and to evaluate the accuracy of DTI. The phantom for diffusion tensor imaging includes: an outer container providing a space; materials for diffusion measurement located in the space of the outer container and formed of bunches of micro-tubes; and materials for fixing located in the space of the outer container to fix the materials for diffusion measurement to a specific location. The micro-tubes in this phantom design may be stems of various plants such as leaves of vegetables or a bamboo stem.

The Medical College of Georgia Research Institute, Inc.'s U.S. Pat. No. 8,134,363 discloses a phantom for use with diffusion MRI comprising a plurality of anisotropic arrays stacked in a plurality of parallel rows to form a macro-array, wherein each of the arrays includes a plurality of typically glass capillaries (ID 10-90 microns) with each of the capillaries holding a first fluid; and a housing, holding a second liquid.

U.S. Pat. No. 8,643,369 describes an anisotropic diffusion phantom for the calibration of any diffusion MR-DTI imaging sequence the form of an array of thin glass plates separated with $H_2O$ layers, wherein the layers have a thickness of about 10 microns.

BrainLAB's U.S. Pat. Publication No. 2006-0195030, now U.S. Pat. No. 7,521,931, discloses a phantom for use with diffusion tensor imaging which includes a container and a plurality of structures within the container. The structures have anisotropic properties, wherein when the phantom is subjected to diffusion tensor imaging, the structures provide data that is recognized as fiber bundles. The structures can be formed, for example, from cloth tape, silk, wood, glass fibers cord (synthetic and viscose) and/or "microfibers".

The Department of Health and Human Services published U.S. Pat. Publication No. 2012-0068699, which discloses a phantom calibration body for calibrating diffusion MRI device which includes a homogeneous aqueous solution that contains a mixture of low molecular-weight and high molecular-weight polymers housed in a container.

Alexander J. Taylor, "Diffusion Tensor Imaging: Evaluation of tractography algorithm using ground truth phantoms," Virginia Tech, May 2004 describes the creation of a physical phantom to evaluate the performance of tractography algorithms, which are used to estimate tissue microstructure. In creating this phantom, Taylor used polytetrafluoroethylene (PTFE) capillary tubing with an inner dimension (ID) of over 300 microns and an outer diameter of over 700 microns. Multiple segments of the tubing were cut, filled with water, and assembled into sheets with a 90 degree crossing pattern. The capillary sheets were placed in a small plastic container and surrounded by gelatin to mitigate air related susceptibility artifacts in the images.

Ching-Po Lin, Van Jay Wedeen, and Jyh-Horng Chen, "Validation of diffusion spectrum magnetic resonance imaging with manganese-enhanced rat optic tracts and ex vivo phantoms," NeoroImage, vol19(2003) 482-495, discusses creation of a phantom to be used to compare the effectiveness of DTI and Diffusion Spectrum Imaging (DSI) for correctly determining the orientation of crossed axonal fibers. Lin used PTFE "microbore" tubing with ID 50 micron and OD 350 micron. Segments of the tubing were filled with water and assembled into sheets. Layers of these sheets were stacked at 90 and 45 degrees in reference to each other in an interleaved fashion. The structures were then secured to a firm plastic plate.

Elisabeth A. H. von dem Hagen and R. Mark Henkelman, as described in "Orientational Diffusion Reflects Fiber Structure Within a Voxel," Magnetic Resonance in Medicine, 48: 454-459 (2002), were possibly the first individuals to evaluate the effectiveness of DTI for determining fiber orientation using a physical model. This phantom also consisted of PTFE "ultramicrobore" tubing having ID 50 micron and OD 350 micron. The capillaries were filled with water by a gluing a 22½—gauge needle to each segment. After being filled, the capillaries were sealed by melting both ends and removing the needle. The capillaries were placed in three different orientations, namely, aligned, coiled, and random and placed inside borosilicate glass tubes. For discussion of similar phantoms see Atiba Fitzpatrick, "Automated Quality Assurance for Magnetic Resonance Image with Extensions to Diffusion Tensor Imaging" Virginia Polytechnic Institute, June 2005.

Lorenz, R., Bellemann, M E., Jenning, J., & Il'yasov, K A., Anisotropic phantoms for quantitative diffusion tensor imaging and fiber tracking validation (2008). Appl Magn Reson. 33, 419-429, disclosed work from the University Hospital Freiberg, Freiberg D E and University of Applied Science Jena, Jena D E, in which four different types of fiber phantoms were used, namely Hemp, Rayon (Diameter 100 Microns), Linen (Diameter 340 microns), and Dyneema (Diameter 200 microns), wherein Dyneema is formed of braided strands of polyethylene fibers. Each of the fibers were used to form fiber bundles under water with the bundle having a cross sectional area of about 450 $mm^2$. Crossing phantoms for similar bundles were formed in a frame and tested. The conclusion of the study was that only the Dyneema bundles served as reproducible phantoms, but these only allowed tracking of the interstitial water due to hydrophobic properties.

Poupon, C., Rieul, B., Kezele, I., Perrin, M., Poupon, F., & Mangin, J F. (2008), New diffusion phantoms dedicated to the study and validation of high-angular-resolution diffusion imaging (HARDI) models. Magnetic Resonance in Medicine, 60, 1276-1283; discloses work developed in part at General Electric Healthcare and Institut d'Imagerie Biomedicale in Gif-sur-Yvette France and utilized 20 micron diameter acrylic fibers bundled together in a two part frame forming a 45 degree and 90 degree crossing phantom and in a fiber density of 1900 fibers/$mm^2$.

The current needs for MRI phantoms for anisotropic imaging for validating and calibrating fiber tracking technologies and systems were also recently elaborated in the May 2014 International Society for Magnetic Resonance in Medicine (ISMRM) meeting, see Michael A. Boss, Thomas L. Chenevert, Daniel P. Barboriak, Mark A. Rosen, Edward F. Jackson, Alexander R. Guimaraes, David E. Purdy, Thorsten Persigehl, Hendrick Laue, Marko K. Ivancevic, Gudrun Zahlmann (2014) QIBA Perfusion, Diffusion, & Flow MRI Technical Committee: Current Status Poster proceedings ISMRM meeting Milan Italy May 2014, (see www.ismrm.org).

Carolin Reischauer, Phillipp Staempfli, Thomas Jaermann and Peter Boesiger (2009) Construction of a Temperature Controlled Diffusion Phantom for Quality Control of Diffusion Measurements; Journel of Magnetic Resonance Imaging 29:692-698 describes a temperature controlled diffusion phantom using dyneema fibers which are braided strands of polyethylene Juneja, Vaibhav, "Novel Phantoms and Post Processing For Diffusion Spectrum Imaging" (2012), UT GSBS Dissertation and Thesis (Open Access) Paper 240.describes a crossing fiber phantom constructed of capillary filled hollow fibers of 50 micron inner diameter and 150 micron outer diameter.

Physical phantoms, as described and discussed above, provide a different balance between ground truth control and realism, to that provided by computer simulations. The above identified patents and patent applications are incorporated herein by reference and these together with the cited papers, and supporting work discussed therein, firmly establish the continued need for effective MRI phantoms for anisotropic and isotropic imaging for validating and calibrating fiber tracking technologies and systems.

SUMMARY OF THE INVENTION

One aspect of this invention is directed to a cost effective, efficient, universal, modular, temperature controlled MRI phantom for calibration and validation for anisotropic and isotropic imaging comprising an outer insulating shell configured to be received within an MRI chamber; an inner shell received within the outer insulating shell; a fluid conduit adjacent the inner shell for selectively receiving temperature controlling fluid or gas cycling there-through; and a series of stacked layers of frames containing test points for the MRI phantom, wherein each layer includes at least one fiducial and further including at least some anisotropic imaging test points in at least one frame and at least one isotropic imaging test point in at least one frame.

One aspect of this invention is directed to a cost effective, efficient, MRI phantom for calibrated anisotropic imaging comprising hollow tubular textile fibers, wherein each hollow tubular fiber has an outer diameter of less than 50 microns and an inner diameter of less than 20 microns, wherein at least half of the hollow tubular fibers are filled with a fluid.

One aspect of this invention is directed to a cost effective, efficient, MRI phantom for calibrated anisotropic imaging comprising hollow tubular textile fibers, wherein at least some of the hollow tubular fibers are filled with a fluid, wherein at least some of the hollow tubular fluid filled textile fibers are formed in fasciculi, also called fascicules, bundles or threads, wherein at least some fasciculi are combined into tracks that are supported in at least one routing frame which includes a plurality of distinct track starting locations at one end thereof and a plurality of aligned track ending locations at an opposed end thereof and tracks extending from the starting locations to the ending locations, wherein substantially all of the tracks end in an ending location that is not aligned with the respective track's starting location.

The phantom of the invention operates at the biologically meaningful range of sub 20 micron hollow fibers that are filled with fluid (e.g. water), that can control the packing density, micron level crossing structure of curves, crossings, merging and kissing in 2 and 3D structures to closely match human tissue. The phantom of the invention uses textile fibers in bundles matching fasciculi and tracts of the human brain. The phantom of the invention can be manufacture with tight precision and with the geometries needed. The phantom of the invention may be manufactured exhibiting the diffusion properties (e.g., the factional anisotropy (FA) and apparent diffusion coefficient (ADC)) in the human tissue range as a commercially viable scale and cost of filling the hollow fibers.

One aspect of this invention is directed to a cost effective, efficient, MRI phantom for calibrated anisotropic imaging comprising hollow tubular textile fibers, wherein at least some of the hollow tubular fibers are filled with a fluid, wherein at least some of the hollow tubular fluid filled textile fibers are formed in fasciculi, wherein at least some fasciculi are combined into tracks that are supported in at least one fixed frame, wherein the phantom includes a plurality of alignment targets visible to the MRI, and wherein the phantom is configured to be worn by a patient in the MRI.

One aspect of this invention is directed to a cost effective, efficient, MRI phantom for calibrated anisotropic imaging comprising an MRI phantom for calibrated anisotropic imaging comprising hollow tubular textile fibers, wherein at least some of the hollow tubular fibers are filled with a fluid, wherein at least some of the hollow tubular fluid filled textile fibers are formed in fasciculi, wherein at least some fasciculi are combined into tracks that are supported in at least one crossing density frame which includes at least three angle fiber crossings across the fixed frame, wherein the angle fiber crossings include a plurality of distinct fiber densities.

One aspect of this invention is directed to a cost effective, efficient, MRI phantom for calibrated anisotropic imaging comprising an MRI phantom for calibrated anisotropic imaging comprising hollow tubular textile fibers, wherein at least some of the hollow tubular fibers are filled with a fluid, wherein at least some of the hollow tubular fluid filled textile fibers are formed in fasciculi, wherein at least some fasciculi are combined into tracks that are supported in at least one crossing density frame which includes at least three angle fiber crossings across the fixed frame, wherein the angle fiber crossings include a plurality of distinct fiber densities.

One aspect of this invention is directed to a cost effective, efficient, MRI phantom for calibrated anisotropic imaging comprising hollow tubular textile fibers, wherein at least some of the hollow tubular fibers are filled with a fluid, wherein at least some of the hollow tubular fluid filled textile fibers are formed in fasciculi, wherein at least some fasciculi are combined into tracks that are supported in at least one a fiber density frame which includes fiber density variations across the fixed frame, whereby the fibers/unit area in the fixed frame are provided at distinct known varied amounts at least three distinct test points across the fixed frame.

One aspect of this invention is directed to a cost effective, efficient, MRI phantom for calibrated anisotropic imaging comprising hollow tubular textile fibers, wherein at least some of the hollow tubular fibers are filled with a fluid, wherein at least some of the hollow tubular fluid filled textile fibers are formed in fasciculi, and wherein at least some fasciculi include interstitial fluid, and wherein hollow tubular fluid and the interstitial fluid is formed of both water and deuterium oxide. Most commonly deuterium oxide will be within the fibers, although deuterium oxide as intersticial fluid is possible.

These and other aspects of the present invention will be clarified in the description of the preferred embodiment of the present invention described below in connection with the attached figures in which like reference numerals represent like elements throughout.

BRIEF DESCRIPTION OF THE DRAWINGS

FIG. 2 is a perspective sectional view of an MRI phantom for calibrated anisotropic imaging according to one embodiment of the invention;

FIG. 4 is a schematic view of an MRI phantom for calibrated anisotropic imaging according to one embodiment of the invention;

FIG. 12D is a perspective view of the frame layer of FIG. 12C; and

FIG. 13 is a sectional perspective view of a frame layer for isotropic test points for the universal, modular, temperature controlled MRI phantom of FIG. 11B.

BRIEF DESCRIPTION OF THE PREFERRED EMBODIMENTS

Figure 1A:
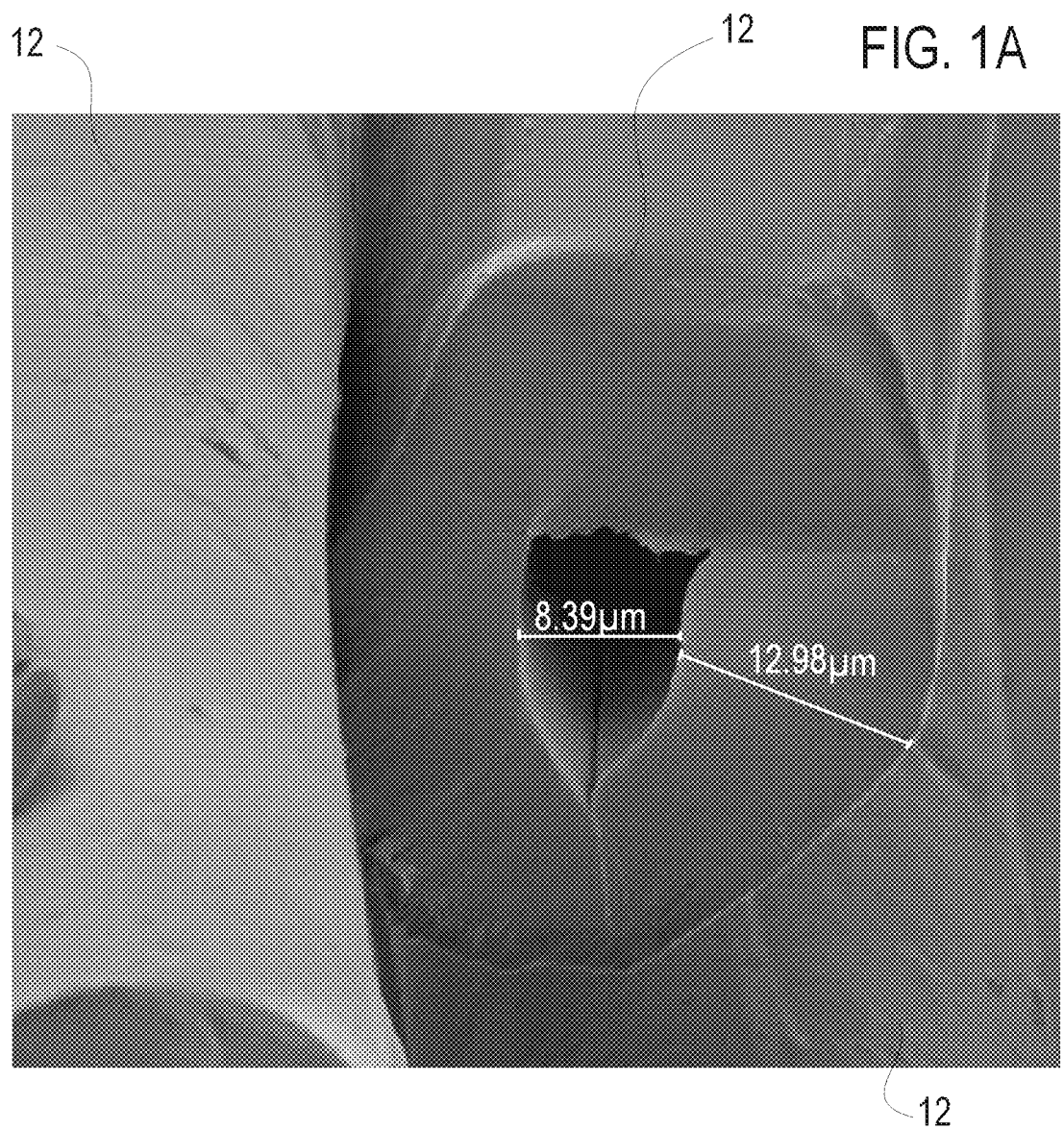
FIG. 1A is a perspective image of a hollow polypropylene fiber for forming an MRI phantom for calibrated anisotropic imaging according to one embodiment of the present invention.

This invention, in one embodiment thereof, is directed to an MRI phantom 10 for calibrated anisotropic imaging comprising hollow tubular textile fibers 12, wherein each hollow tubular fiber 12 has an outer diameter of less than 50 microns and an inner diameter of less than 20 microns, wherein at least half, and preferably at least 70%, of the hollow tubular fibers are filled with a fluid 14. Fluid, within the meaning of this application includes liquids (e.g., water and deuterium oxide) and gels (e.g., hydrogel), but not gasses. The fluid filled hollow tubular textile fibers 12 for calibrated anisotropic imaging may form part of a universal, modular, temperature controlled MRI phantom 10, shown in FIGS. 11A-E, for calibration and validation for anisotropic (HDFT) and isotropic imaging (standard diffusion). Universal within the meaning of this application defines that the MRI phantom 10 is configured to fit substantially any MRI system and can be used for calibrated anisotropic imaging and calibrated isotropic imaging. Modular within the meaning of this application defines that the MRI phantom 10 is configured to receive distinct user selected test points therein, which preferably includes the fluid filled hollow tubular textile fibers 12 with multiple test points for calibrated anisotropic (HDFT). Temperature controlled references that the MRI phantom 10 is configured to maintain a substantially constant temperature, within +−8 degrees, throughout the MRI testing. The cost effective, efficient, universal, modular, temperature controlled MRI phantom 10 for calibration and validation for anisotropic and isotropic imaging comprises an outer insulating shell 200 configured to be received within an MRI chamber; an inner shell 210 received within the outer insulating shell 200; fluid conduits 220 adjacent the inner shell 210 for receiving temperature controlling fluid or gas cycling there-through; and a series of stacked layers 230 of frames 20 containing test points for the MRI phantom 10, including at least some anisotropic imaging test points in at least one frame 20 and at least one isotropic imaging test point in at least one frame 20.

The details of the universal, modular, temperature controlled MRI phantom 10 for calibration and validation for anisotropic and isotropic imaging of FIGS. 11A-E, is better explained following the description of the MRI phantom 10 of the present invention for calibrated anisotropic imaging comprising the fluid filled hollow tubular textile fibers 12, detailed in connection with FIGS. 1A-10C.

The textile fibers 12 used in selected frames 10 of the MRI phantom 10 of the present invention may be effectively formed from polymer fibers. These hollow textile fibers 12 exhibit the required characteristics and represent a key step for creating a phantom 10 that properly mimics the human brain for anisotropic imaging. These polymer fibers 12 generally may include polyamide nylon; PET or PBT polyester; phenol-formaldehyde (PF) polyvinyl chloride fiber (PVC) vinyon; polyolefins (PP and PE) olefin fiber; acrylic polyesters; pure polyester PAN fibers, aromatic polyamids (aramids) such as Twaron, Kevlar and Nomex; polyethylene (PE), eventually with extremely long chains/HMPE (e.g. Dyneema or Spectra); Elastomers, e.g. spandex; urethane and polyurethane fibers; and Elastolefin. In the selection of fiber material of fibers 12, the material hydrophobicity is very important as hydrophobic materials have a higher fractional anisotropy. Further it is desirable if the material configuration or structure is similar to the axons with regard to MRI response, such that the hollow synthetic fibrous materials can effectively mimic the configuration of the axons, wherein each hollow tubular fiber 12 has an outer diameter of less than 50 microns and an inner diameter of less than 20 microns. The outer diameter of the fibers 12 is generally less than 30 microns and often less than 25 microns, or 20 microns. The inner diameter may also be less than 15 microns, and even 5 microns or less.

Fibers 12

Figure 1B:
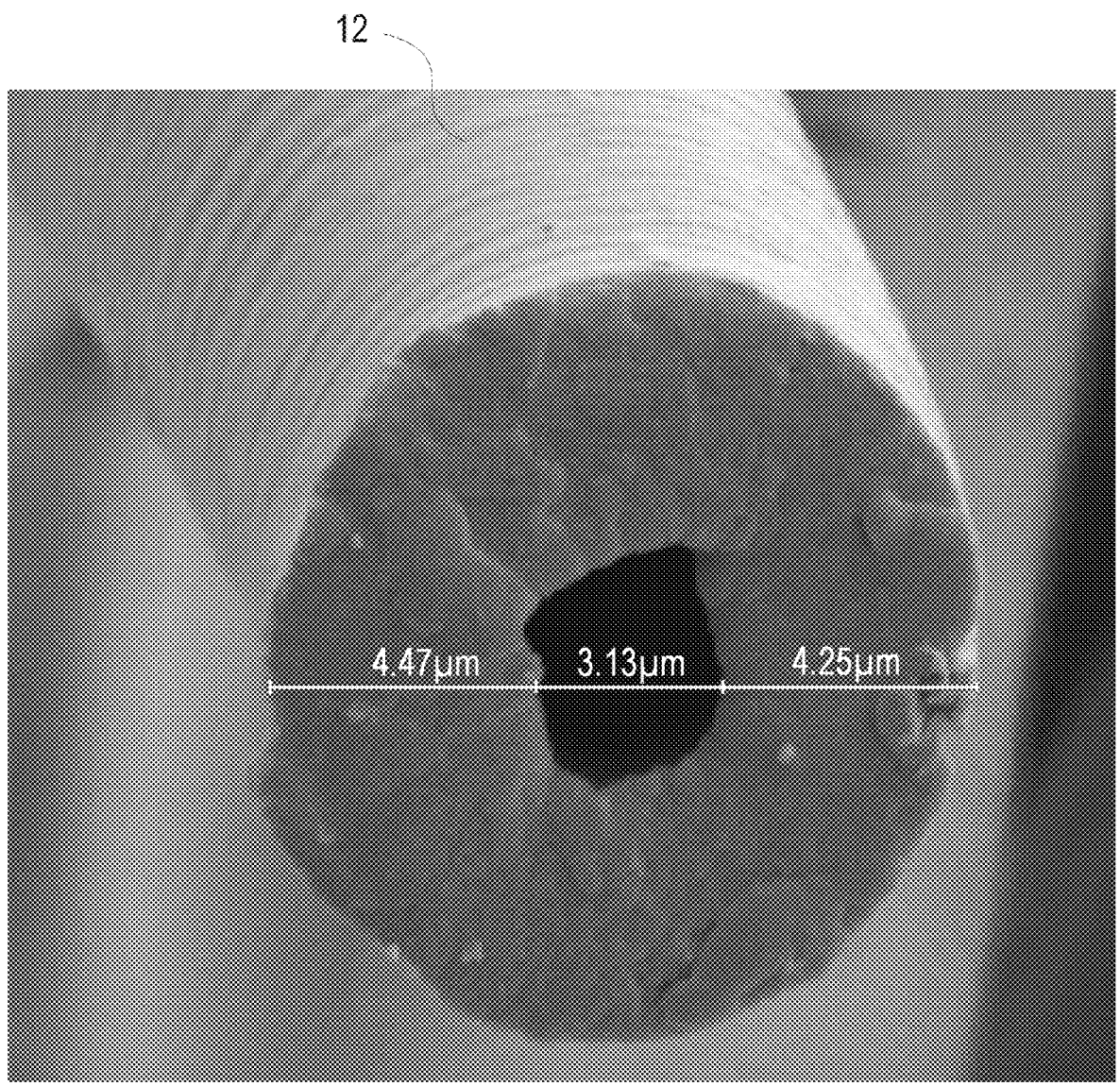
FIG. 1B is a perspective image of a hollow polyester fiber for forming an MRI phantom for calibrated anisotropic imaging according to one embodiment of the present invention.
Figure 1C:
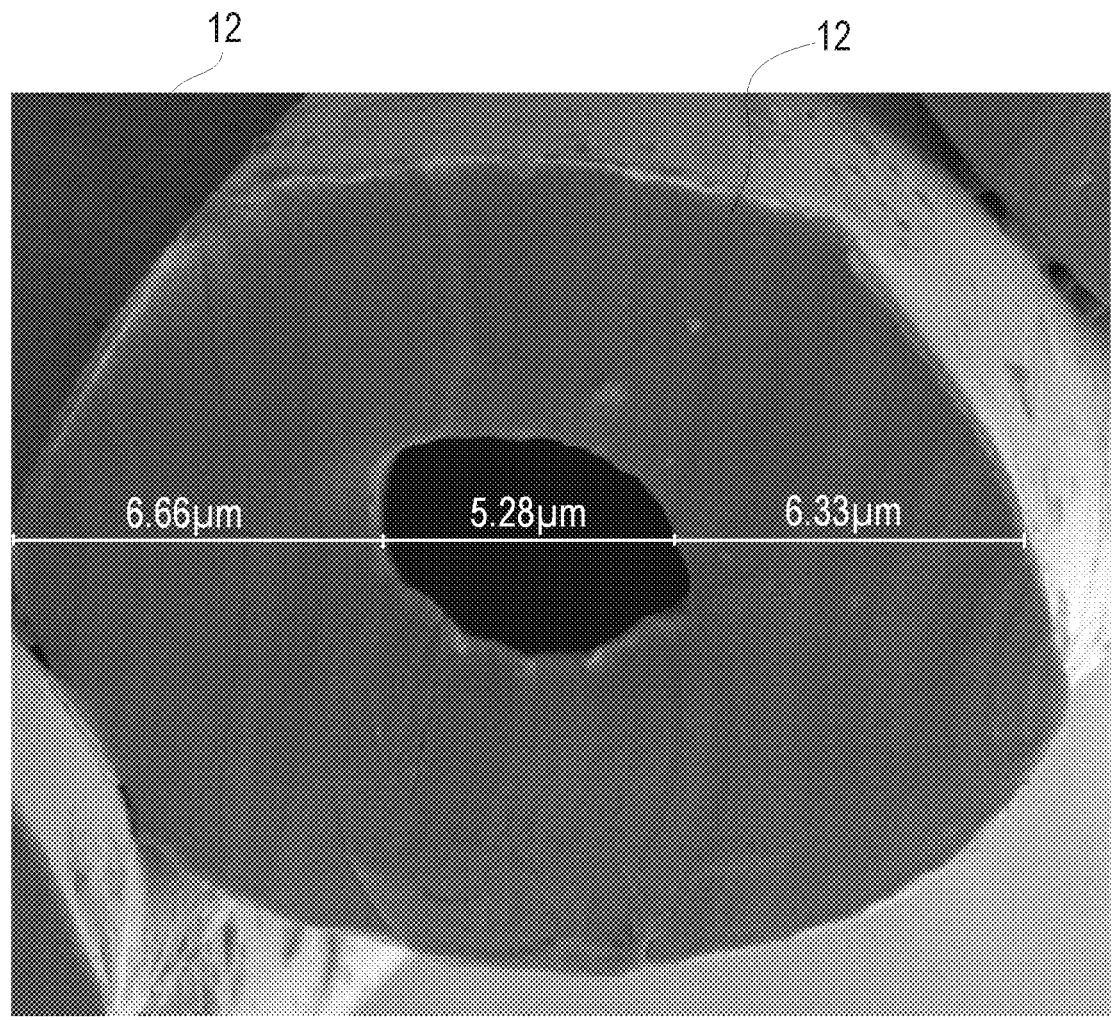
FIGS. 1C and D are perspective images of a hollow polyamide fiber for forming an MRI phantom for calibrated anisotropic imaging according to one embodiment of the present invention.
Figure 1D:
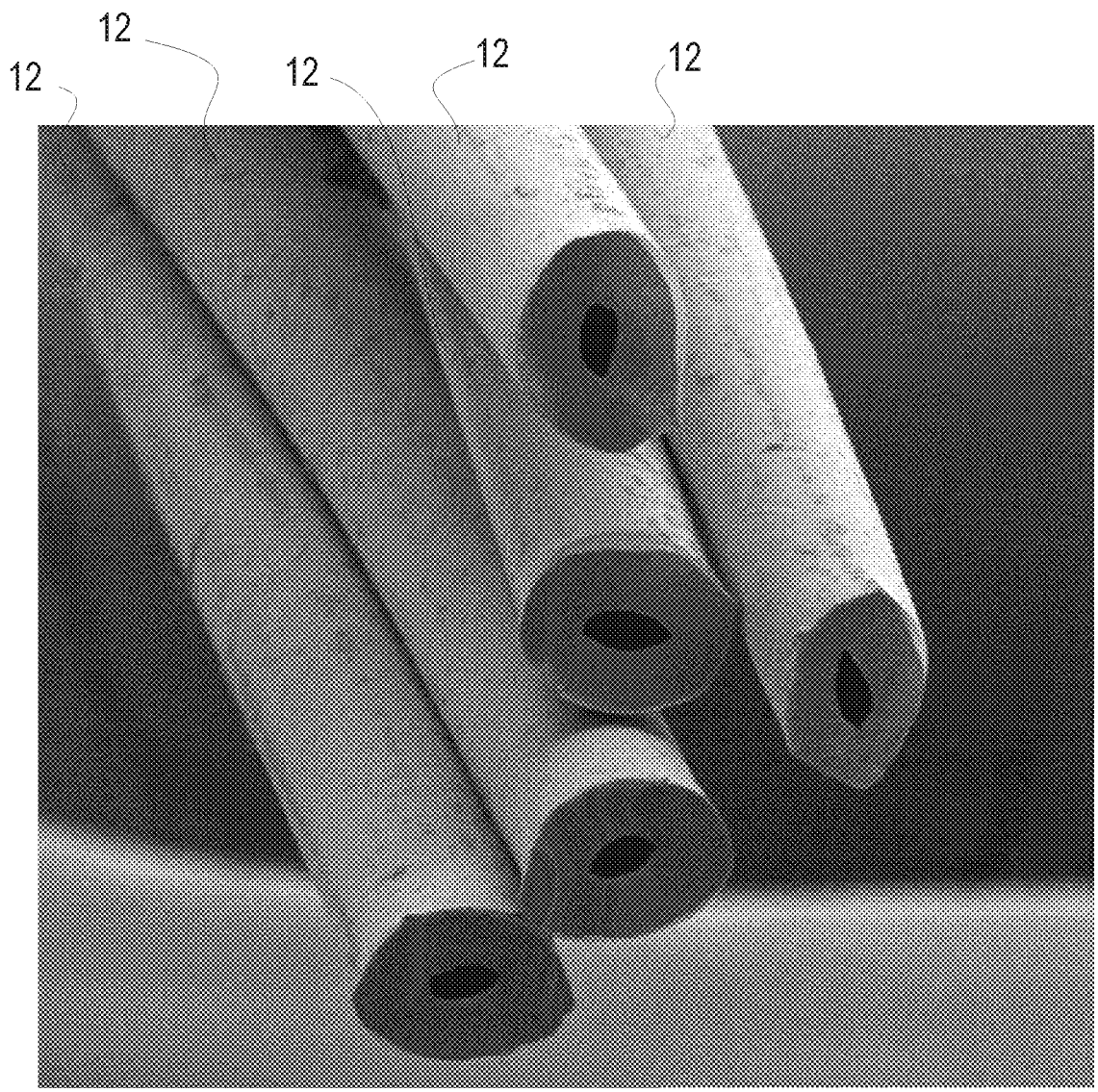

FIGS. 1A-D illustrates representative hollow polymer textile fibers 12 useful for forming filled fluid fibers 12 for anisotropic imaging in the phantom 10 of the present invention. FIG. 1A is an image of polypropylene based fiber 12 for forming the phantom 10 of the present invention wherein the inner diameter measured as shown is about 8.4 microns and the wall diameter is 13 microns. FIG. 1B is an image of polyester based fiber 12 for forming the phantom 10 of the present invention wherein the inner diameter measured as shown is about 3.15 microns and the wall diameter is 4.36 microns. FIGS. 1C and D are images of polyamide based fiber 12 for forming the phantom 10 of the present invention wherein the inner diameter measured as shown is about 5.3 microns and the wall diameter is about 6.5 microns.

Hollow fibers similer to fibers 12 of phantom 10 are often used in membranes for ultra filtration, artificial kidneys, artificial lungs, oxygenation devices etc. Round, squares and trilobals are examples of geometries used to produce hollow fibers and which is discussed further in Omeroglu, S. Karaca, E., & Becerir, B. (2010), Comparison of Bending, Drapability and Crease Recovery Behaviors of Woven Fabrics Produced from Polyester Fibers Having Different Cross-sectional Shapes, Textile Research Journal, 80, 1180-1190.

The hollow fibers 12 may be produced by extrusion technique with a spinneret forming the desirable hollow configuration. Thus there is an additional dimension from ordinary fibers, namely the inner diameter that is not present in many textile fibers. This formation is discussed further in Oh, T., Lee, M., Kim, S., & Shima, H. (1998). Numerical Simulation of the Melt Spinning of Hollow Fibers. Textile Research Journal, 68, 449-456. The spinneret geometry, coagulant flow-rate, polymer solution viscosity and flow rate, and air gap affect the geometry of the hollow fibers. The final fiber size is determined by main factors as the draw ratio, which controls the desired outer diameter; the polymer-to-bore volumetric flow rate, which controls the ultimate outer-to-inner fiber diameter ratio; and, the dimensions of the annular spinneret hole. For further detailed discussion see Su, Y. (2007). Theoretical Studies of Hollow Fiber Spinning Thesis for Doctor of Philosophy Degree in Engineering. The University of Toledo.

Filling Fibers 12 with Fluid 14

One important aspect of the invention is filling the fibers 12 with fluid 14, namely water ($H_2O$) or deuterium oxide ($D_2O$), also called heavy water. The filling of the fibers 12 is not a trivial matter due to the small diameter of the inner diameter and the hydrophobic material. In order to obtain desired MRI results, at least half and preferably at least 70% of the fibers 12 of the phantom 10 will be filled with fluid 14. The 50% fill rate is believed to be the minimum to yield an effective MRI test point associated with filled fibers 12, and 70% is a more meaningful minimum based upon the desired result of yielding an effective MRI test point associated with filled fibers 12. A production standard for verified filling procedures of 80%, 90%, 95% and higher fill rate may be used to verify the effectiveness of the filling procedure (rather than a using a lower percentage that is associated with the effectiveness of the MRI test points themselves), and these higher fill rates are possible with the following procedures. Several considerations should be taken into account in filling the fibers 12. First removing impurities from the fluid 14 via passing fluid 14 through one or more micro-filters can facilitate filling, as can controlling the filling environment (i.e. a dust free/minimal dust environment, such as a clean room or pseudo-clean room), as entrained dust particles may be larger than the inner diameter or sufficient in size to hinder filling. Pressure assisted filling including positive pressure on the fill side (via plunger arrangement or other pressurized source of fluid 14) and possibly reducing pressure on the other side of the fiber 12 can further be implemented to facilitate the filling process. Centripetal force may be utilized with the fibers 12 located along a rotating disc and secured to a filling hub, whereby the centripetal force will increase from the center to help move the fluid 14 along the fibers 12.

In addition to these considerations for facilitating filling of fibers 12, some consideration is made to the original manufacturing and shipping of the fibers 12. Specifically, steps are avoided that introduce inner diameter restrictions, i.e. crimps in the fibers 12. As discussed below, the individual fibers 12 will be grouped into fascicule 16, which can also be called threads or bundles. In textile manufacturing using these hollow fibers, such threads are commonly formed as yarns of many fibers (e.g., 64). Conventional winding tension on the yarns can crimp the outer layer of fibers 12 and detrimentally effect filling of fibers 12 with fluid 14 in the present invention. It is still possible for fascicule 16 to be formed through larger sets of fibers 12, provided this does not introduce an undesired MRI artifact and they do not crimp any of the fibers 12.

For relatively short lengths of fibers 12 and fascicule 16, capillary action can effectively be used for filling the desired fibers 12 with fluid 14. The simplest technique for filling fibers 12 with capillary action is to submerge the fibers 12 within the desired fluid 14 for a desired orientation. A fiber holding frame can be implemented to assist in holding the fibers 12 straight to facilitate capillary action and to allow for a desired orientation within the fluid 14. Naturally capillary action filling does not require the complete submersion of the fibers 12, as such can be accomplished if only one end of fibers 12 is submerged within the fluid 14. Capillary filling action of the fibers 12 can be optimized through the combined use and/or consideration of short lengths of fibers 12, filtering of filling fluid 14 (distilled water, deuterium), treating of filling fluid for viscosity adjustment with MR compatible added materials, pressure control to facilitate capillary action, temperature to facilitate capillary action, sufficient dwell time for completion of capillary action, orientation of the fibers to facilitate capillary action, pre-treatment of fibers (e.g., cleaning) to facilitate capillary action, control of cutting of fibers to maintain opening that facilitate capillary action (do not crimp or minimize opening), and utilization of textile manufacturing techniques of hollow fibers that minimize knots, twisting, kinking or the like that otherwise inhibits the fiber 12's lumen.

The use of capillary action for fluid filling allows for the possibility of forming the desired test pattern or test block of fibers 12 and fascicule 16 prior to the filling procedure (referenced as making dry test blocks), and then followed by filling, generally by submersion of the test block within the fluid 14. Thus the method of building an MRI phantom 10 with capillary action filled hollow fibers 12 may effectively comprise the step of making dry test blocks or patterns with fibers 12, followed by filling the fibers 12 of the test pattern/block with fluid 14 via capillary action and then followed by quality control techniques to verify filling (e.g. visual of significant sample size). The quality control technique may use image analysis to verify filling via visual contrast. Alternatively the fibers 12 may first be filled with fluid 14 via the capillary action and the filling procedure checked/verified and then the test pattern formed with the verified filled blocks. A final process arrangement is to fill the fibers 12 then form the test blocks, then verify the filling such as by MRI image analysis. Regardless or the order, capillary action has proven effective for filling fibers 12, but verification of the filling procedure is still desirable following filing either before or after the test block is formed.

Figure 8A:
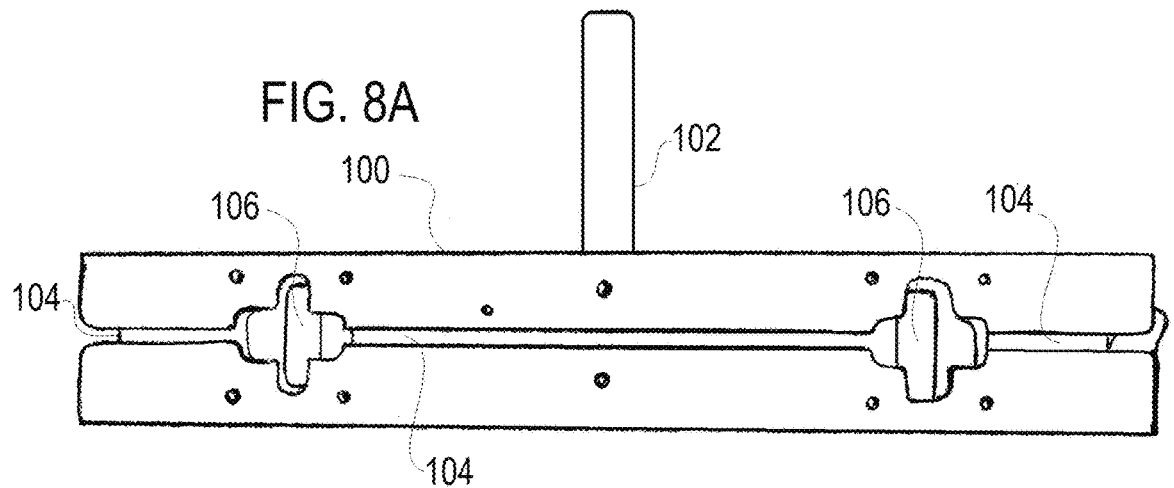
FIG. 8A is a side perspective view of a winding jig or core to assist in filling the hollow textile fibers used in the MRI phantoms for calibrated anisotropic imaging according to the invention.

Longer fiber 12 or fascicule 16 lengths may not be appropriate for capillary filing. Another effective process for filling the fibers 12 useful for longer fibers 12 is described in connection with FIGS. 8A-8E. FIG. 8A illustrates a rotational jig or core 100 to assist in filling the fibers 12. The core 100 includes a shaft 102 that can be coupled to a motor and encoder to count the wraps. The core 100 includes a groove 104 around the periphery within which the fibers 12 are wrapped. The core 100 include two pairs of gasket molds 106 on each side of the core 100 which are used to form silicone gaskets 108 as will be described. In operation the fibers 12 are wrapped around the core 100 within the groove 104. In this embodiment the fibers 12 are grouped in fascicle 16 and the fascicle 16 is being wrapped around the core 100 within the groove 104.

Figure 8B:
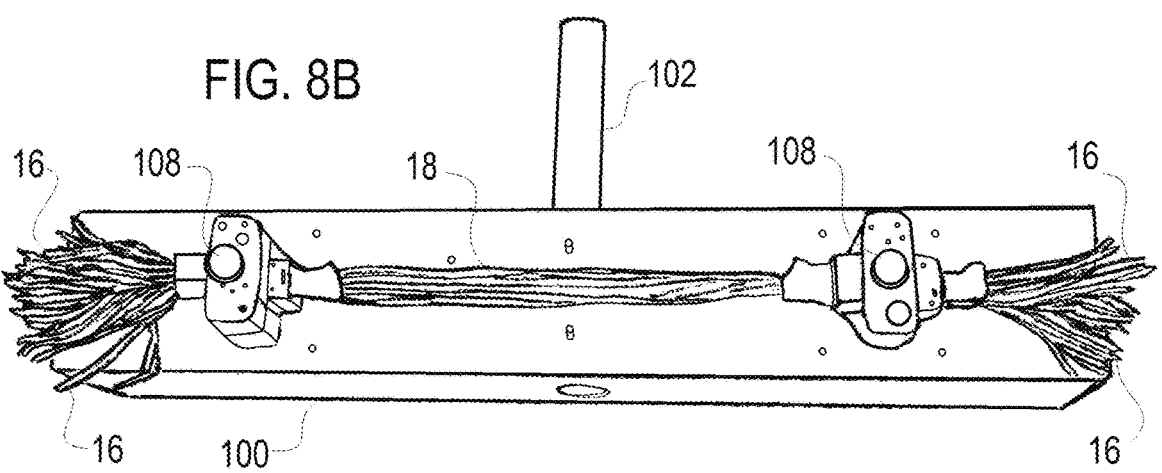
FIG. 8B is a side perspective view of the core of FIG. 8A and an associated untrimmed, unfilled track of fascicules of hollow fibers used in the MRI phantoms for calibrated anisotropic imaging according to the invention.
Figure 8C:
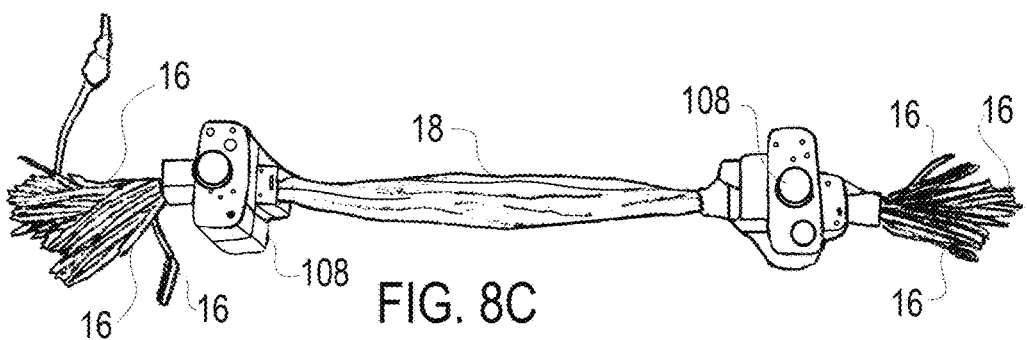
FIG. 8C is a side perspective view of the untrimmed, unfilled track of fascicules of hollow fibers of FIG. 8B.

With every wrapping or every few wrappings of the fascicle 16 formed of the fibers 12, the fibers 12 are coated with silicone, or similar anchor substance, in the area of the molds 106 to assure the fibers 12 are coated and the gasket 108 is complete when formed. Once the number of wrappings is sufficient to form the desired track 18, the wrapping ceases. Then outer mold halves are coupled to the core 100 above each mold 106 and silicone is injected into the molds 106 to form the complete gaskets 108. The fascicles 16 may be severed at the ends of the core 100 to form two unfilled, untrimmed tracks 18 each with a pair of silicone gaskets 108 as shown in FIG. 8B. FIG. 8C shows an unfilled, untrimmed track 18 with a pair of silicone gaskets 108 removed from the core 100.

Figure 8D:
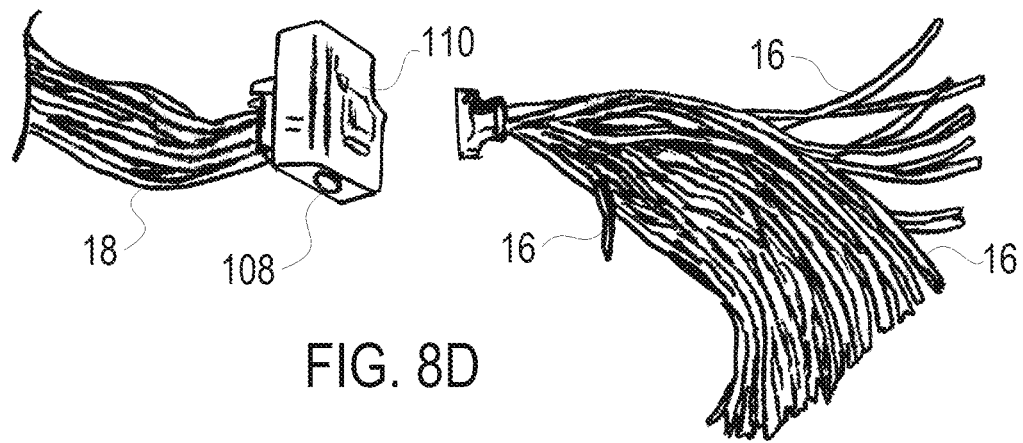
FIG. 8D is a side perspective view of the trimmed, unfilled track of fascicules of hollow fibers of FIG. 8C.
Figure 8E:
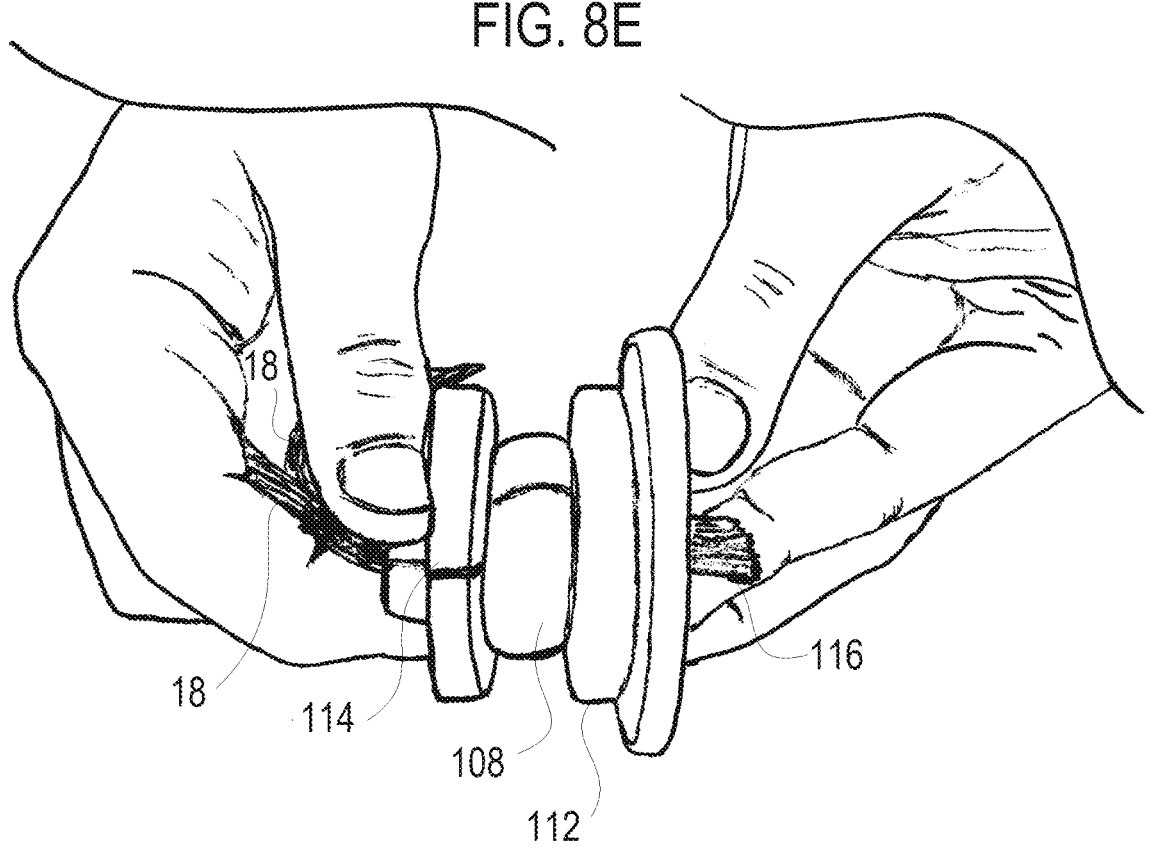
FIG. 8E is a side perspective view of the trimmed, unfilled track of fascicules of hollow fibers of FIG. 8D mounted for filling.

The silicone gasket 108 serves several purposes, the first of which is to provide a supporting substrate for trimming the fibers 12 such that the individual fibers remain open and are not crushed, as the cannot be filled if they are crushed. The unfilled, untrimmed track 18 with a pair of silicone gaskets 108 are trimmed by cutting through the gaskets 108 as shown in FIG. 8D and the trimmed filling surface 110 will exhibit the open hollow fibers 12 surrounded by silicone forming gasket 108. Cutting perpendicular to the fibers 12 with a sharp blade is preferred.

The second purpose of each gasket 108 is to allow for attachment of that trimmed filling surface 110 within a filling chamber of a coupling member 112. The gasket 108 may provide a face seal against a corresponding surface of the coupling member 112 or the peripheral edge of the gasket 108 can seal against an inner peripheral edge of the coupling member 112, or both. A clamping member 114 will help secure the gasket 108 in place with clamping bolts (not shown) to provide desired coupling pressure. The coupling member 112 includes a conduit tip 116 to attach to a source of pressurized fluid 4 which has been filtered, and/or at the trailing end the gasket 108 may attach to a coupling member 112 in which the tip 116 is coupled to a vacuum source if desired. The fibers 12 within track 18 may thus be filled simultaneously and efficiently.

Following filling of the fibers 12, the distal end of the track 18 of the fibers 12 may be sealed such as by dipping in silicone, thereby closing the open ends of the fibers 12 at the distal end. The remaining open end at the proximal end can then be removed from the filling unit and sealed in a similar manner to form the filled hollow tubular textile fibers 12 of the phantom 10. As noted above, a number of additional aspects may be used to facilitate filling, such as vacuum/lower pressure on the opposed open ends during filing, centripetal force, temperature controls to facilitate filling, additives that facilitate filling the small diameter hollow fibers 12. The extraneous parts of the gaskets 108, such as those extending beyond fascicules 16 used for the earlier sealing may be trimmed, if desired. Other closing techniques may be considered such as crimping, heat sealing or combinations thereof. The advantage of crimping and heat sealing and combinations of these is that neither introduces another MRI signature or artifact into the system. In the discussion below the usable portion of the filled fibers 12 will be that located between the gaskets 108, although the (trimmed) gaskets 108 may also serve to assist in mounting of the track 18 to the desired fixed frame 20 of the phantom 10.

The core 100 described above included a pair of usable tracks 18 on each side. Alternatively the core 100 may be modified to include a single gasket mold 106 and the operation can wrap the long fiber 12/fascicles 16 around the core 100 having a circumference generally of the desired fiber 12 length. The wrapped fibers 12 will be coated with silicone periodically at a small segment of the core 100 with the single mold 106. When the fibers 12 are present in a desired amount for the filling apparatus, such as sufficient to form a track 108, the single gasket 108 is formed and the fibers 12 are cut within in the middle of the single silicone gasket, thereby forming an unfilled track 18 with two silicone gaskets 108 at each end. The trimmed unfilled track 18 may be filled as described above. As noted above, a number of additional aspects may be used to facilitate filling, such as vacuum/lower pressure on the opposed open ends during filing, centripetal force, temperature controls to facilitate filling, and additives that facilitate filling the small diameter hollow fibers 12.

Figure 9A:
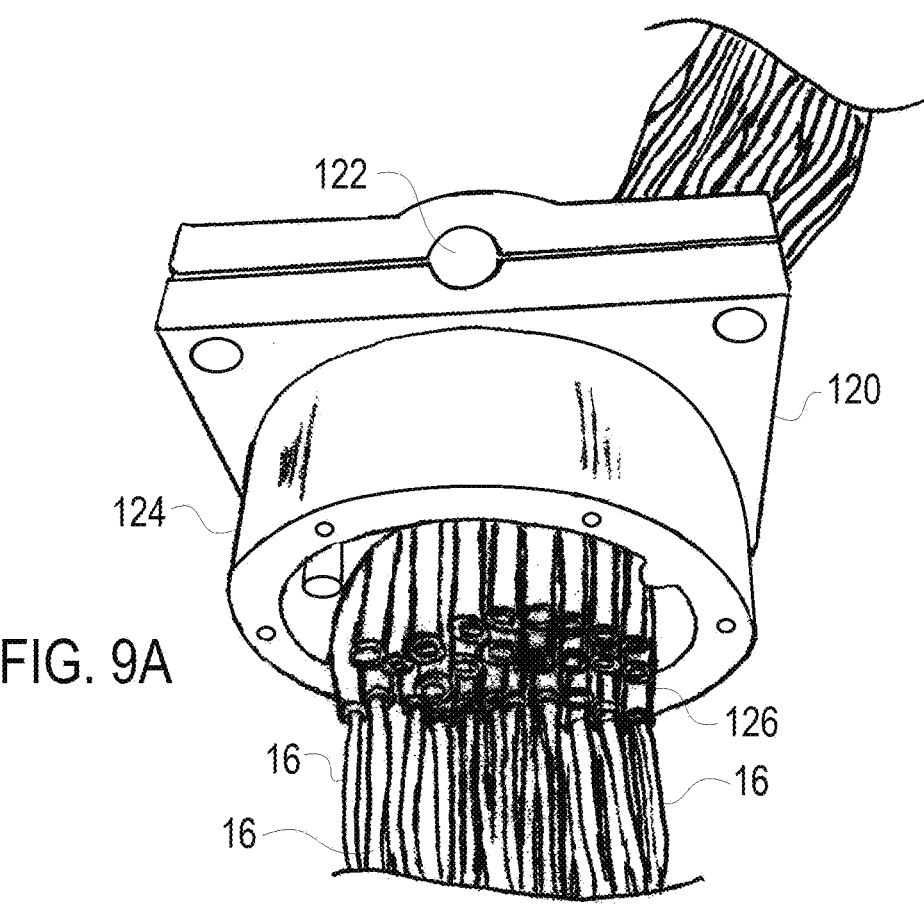
FIGS. 9A and B are perspective views of in integrated mold and coupling member with threaded fascicule there through which assists in filling the hollow textile fibers used in the MRI phantoms for calibrated anisotropic imaging according to the invention.
Figure 9B:
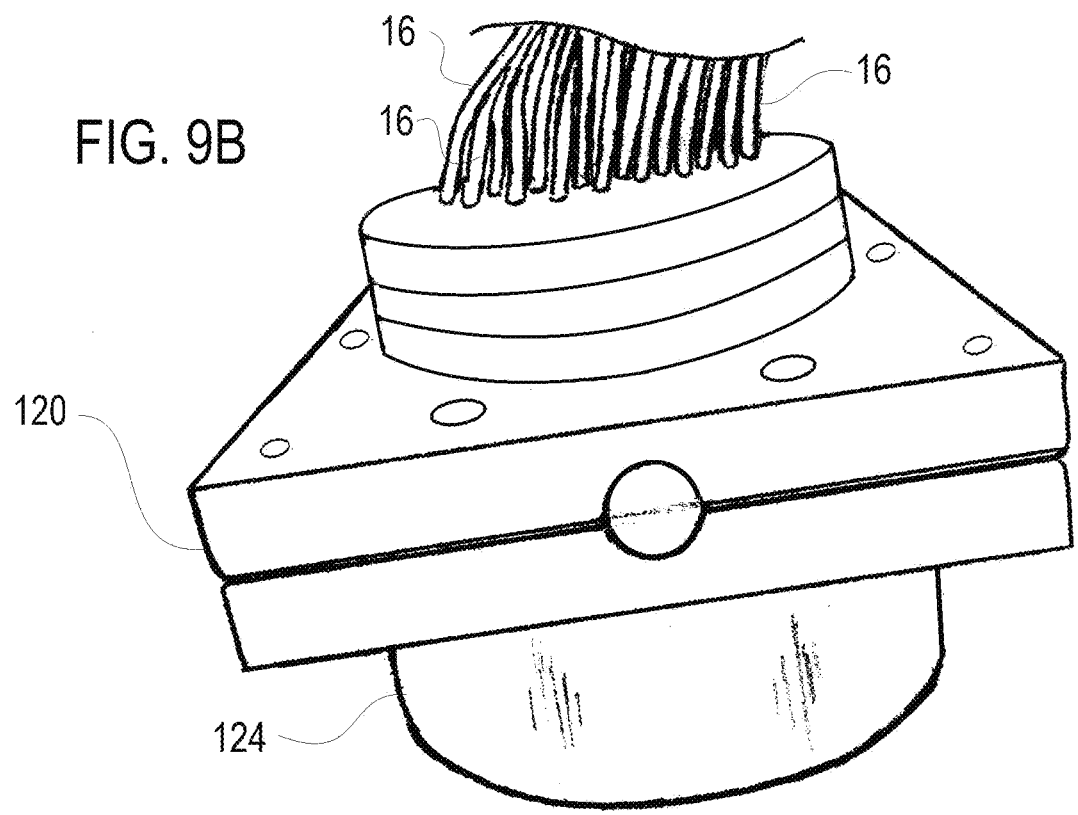

FIGS. 9A and B illustrate an alternative filling arrangement that is by groups of individual fascicules 16, and this is also useful for longer runs or lengths of fibers 12. In this filling arrangement a two piece mold 120 with top filling opening 122 and which further includes a series of individual openings there-through on the face thereof in which individual fascicles 16 are advanced. One side of the mold 120 includes a cylindrical coupling member 124 to be coupled to a fluid source. Around each opening for the individual fascicules 16 are plastic cylindrical mold extensions 126. Once the fascicules 16 are threaded through the openings, the mold 120 is filled with silicone with the mold extensions 126 serving to allow the silicon to advance around each individual fascicule 16. Then the end is trimmed by slicing through the mold extensions 126, the silicon and each individual fascicule 16 to form the open end filling face 110 within the coupling member 124. The coupling member 124 can be coupled to a source of fluid 14 and the fascicules 16 filled as above. The distal end may be sealed in any convenient fashion as described above. The sealing of the end with mold 120 can be accomplished downstream from the mold 120 at the proximal end and the mold 120 then removed from the fascicules 16/track 18. The mold 120 of FIGS. 9A and B allows the filling of individual fascicules 16 as desired and may better accommodate larger variations in length of filled fibers 12.

Other modifications of these filling techniques may also be used as well as combining features thereof. There should be validation of the filling process regardless of the filling process utilized (or whether it is before or after the test blocks are formed), which can be accomplished by a number of methods. Weighing of the filled fascicule 16 may be the most efficient. Direct examination of a representative sample of fascicules 16 is also an acceptable validation method, wherein submersion of distal ends of fascicules 16 and associated fibers 12 in contrasting media, such as oil or other similar substance, may assist in direct observations of water filling. MRI image analysis of the filled tubes and/or the formed test blocks may be acceptable as a verification process. As noted above at least ½ and preferably at least 70% fibers 12 of the phantom 10 of the present invention are filled with fluid 14 as minimums for forming effective test points for filled fibers 12, and the above filling techniques easily allow for 80%, 90% and 95% fill rates to be easily accomplished without undue costs. The higher fill rates 80%, 90% and 95% may be used as production standards to yield more definitive phantoms 10.

Other filling techniques than described above may be implemented, such as filling individual fibers 12 at manufacturing. Further, although filled in a combined fascicule 16 or track 18, the individual filled fibers 12 may later be separated in a specialized phantom construction as desired.

As noted above the fibers may be filled with water or deuterium oxide. Other possibilities include water with substances to improve viscosity for filling. Further other elements are possible to be added to the water outside of merely to facilitate filling of the fibers 12. For example materials suspended in water (e.g. iron to examine susceptibility in vascular shapes), provided the suspended particles do not detrimentally effect filling and are suitably MRI compatible. T Restricted and Hindered Water Differentiation The phantom 10 for calibrated anisotropic imaging using fluid 14 filled fibers 12 provides precise and repeatedly manufactured simulated axonal diffusion structures to separate and quantify simulated intra-axonal water (i.e. fluid 14 within the fibers 12), which has been termed "restricted" in the MRI literature, and simulated extra-axonal water, also called interstitial fluid, (i.e. fluid between fibers 12 in a given fascicule 16), wherein water between the axons is termed "hindered" water within the MRI literature, and free water or isotropic diffusion. The phantom 10 for calibrated anisotropic imaging using fluid 14 filled fibers 12 is composed of hollow fibers 12 which are micron-scale textiles manufactured and arranged in test blocks or patterns in controlled crossing and packing densities in two and three dimensions. The goal is to provide ground truth quantification of axonal tract structures, as well as to quantify accuracy and interpretability of diffusion measurements across vendors, instruments, acquisition, and analysis procedures.

The phantom 10 for calibrated anisotropic imaging using fluid 14 filled fibers 12 of the invention provides the ability to measure both the simulated intra-axon (water 14 within fibers 12) and extra-axon water (water between fibers 12) to allow quantification of water that is intra-axonal that allows estimation of the axonal areas of a tract 18 and the integrity of the fibers 12. The measurement of intra-axonal water is believed to be critical in the detection of pathologies, such as traumatic brain injury (TBI), with diffuse axonal injury (DAI) that causes intra-axonal water which is a serious often permanent problem, and increases intra-axonal water through edema often a transitory problem. It is believed to be important that the MRI scanner sensitivity to these two types of water change in a tract can be determined. The concept of intra-axonal water is referred to in the literature (see Assaf, Y. and P. J. Basser, *Composite hindered and restricted model of diffusion (CHARMED) MR imaging of the human brain*. Neuroimage, 2005. 27(1): p. 48-58) as restricted water. That is the water diffusion is restricted by the tube walls to only diffuse in one dimension along the core of the tube. This is, in fact, the key physical feature that allows anisotropic diffusion imaging to selectively image, and to non-invasively quantify, axonal tissue from other tissue. Axons as a tissue type have enormous diameter to length ratios (e.g., 1 micron diameter 10 cm length hence a 10,000 to one ratio). This high ratio allows the MRI machine to be tuned to measure axonal water selectively and not have the measurement confounded by all the other types of water in the brain (or spine) by the many cells intercellular water chambers. However there is a second type of water, namely the extra-axonal water or hindered water. This is the water between the axons. Depending on the compaction of the axons, the spacing between the fibers 12 can closely mimic the diffusion of the intra-axonal (restricted water) but as the extra-axonal water exceeds the intra-axonal water the anisotropic diffusion rapidly drops. It is believed to be critical for an MRI system to accurately measure the axonal integrity of a tract (as in TBI induced diffuse axonal injury) to distinguish intra-axonal water from extra-axonal water effects.

The phantom 10 for calibrated anisotropic imaging using fluid 14 filled fibers 12 according to the present invention is the first phantom technology that supports this critical measurement capability.

Filling the 20 micron, and lower, inner diameter fibers 12 with fluid 14 provides ground truth for the presence of restricted water (water within simulated axons or fibers 12). In contrast, filling selected fibers 12 with $D_2O$ alters the Larmor resonance frequency of the water molecules, eliminating the restricted water signal from the MRI image without altering the chemical or structural properties of the fiber 12. This allows, for the first time, the opportunity to scan the same simulated axonal structures formed by fibers 12 with the restricted water present ($H_2O$ filled) or "removed" ($D_2O$ filled).

The phantom 10 will provide a "ground truth" value for variables used to model diffusion in dMRI, with direct relationship between fiber 12 construction and anatomical structures (e.g., similer/overlapping tube diameters, tract shapes, and interstitial spaces and fluids). This phantom 10 allows the quantification of measurement error in the pipeline. The textiles forming fibers 12 are stable, such that they can be disassembled from the phantom 10 and re-measured to verify maintenance of the water content over years of storage and use.

It is noted that the theoretically most effective metric for detecting TBI is the quantification of loss of intra axonal water that is lost in diffuse axonal injury (DAI, the hallmark of TBI). Thus in HDFT the goal is to quantify, for a given patient's tract, the percentage of loss (10%, 20%, etc of expected intra axonal water in a tract). It is critical that such systems do not falsely interpret other factors (edema, brain size, tract shape variation, shifted crossing locations) as axonal volume loss. The phantom 10 for calibrated anisotropic imaging using fluid 14 filled fibers 12 allows for validation of the HDFT system and calibration of the particular MRI system.

Phantom 10

FIG. 2 shows the construction of a modular MRI phantom 10 for calibrated anisotropic imaging comprising hollow tubular textile fibers 12 filled with a fluid 14, typically water. The textile fibers 12 are formed in fascicle 16 as discussed above and fasciculi 16 are combined into tracks 18 that are supported in fixed frames 20 within the phantom 10. The particular number of fibers 12 in each of the threads or fasciculi 16 may largely depend upon manufacturing and filling criteria, but 64 fibers per fascicule 16 has been effectively used. The number of fasciculi 16 within a track 18 depends upon the size of the fascicule 16 and the desired size of the track 18 for the intended simulation. The phantom 10 for calibrated anisotropic imaging using fluid 14 filled fibers 12 of FIG. 2 is formed as a frusto-spherical shell mounting a plurality of fixed frames 20. The frusto-spherical shape allows for easy mounting within an MRI. The interior of the shell can be filled with water, or heavy water, which can serves as the interstitial fluid between fibers 12 of fascicule 16. As noted above, selective filling of fibers 12 with heavy water allows for differentiation between hindered and restricted fluid.

The fixed frames 20 will have distinct configurations depending upon the desired phantom component being constructed, providing the modular aspect to the phantom 10 of FIG. 2. All of the fixed frames 20 are formed out of material acceptable for the MRI environment that does not create artifacts in the scanned image, except for the inclusion of desired fiducial elements on the frame 20. The fixed frames 20 described herein will allow for an easy mechanism to obtain the desired compression of the tracks 18 of fascicules 16 of fibers 12. For most configurations the fibers 12 need to be compressed to at least 4× the maximum compression volume, which is the volume in which substantially all of the interstitial or extra-axonal water is removed from between the fibers. Some MRI technologies may have difficulty tracking above 2× the maximum compression volume. The fixed frames 20 are typically formed of two main bodies that are bolted together via nylon bolts or the like. In addition to clamping the frame portions together the bolts may be constructed to form fiducial elements for the phantom 10. Three dimensional printers allows for rapid production of new frames 20 in any desired configuration provided the printing material does not introduce undesirable MRI artifacts. Changes to specific fixed frames 20 are thus easily made.

Fiber Crossing Frame

Figure 3C:
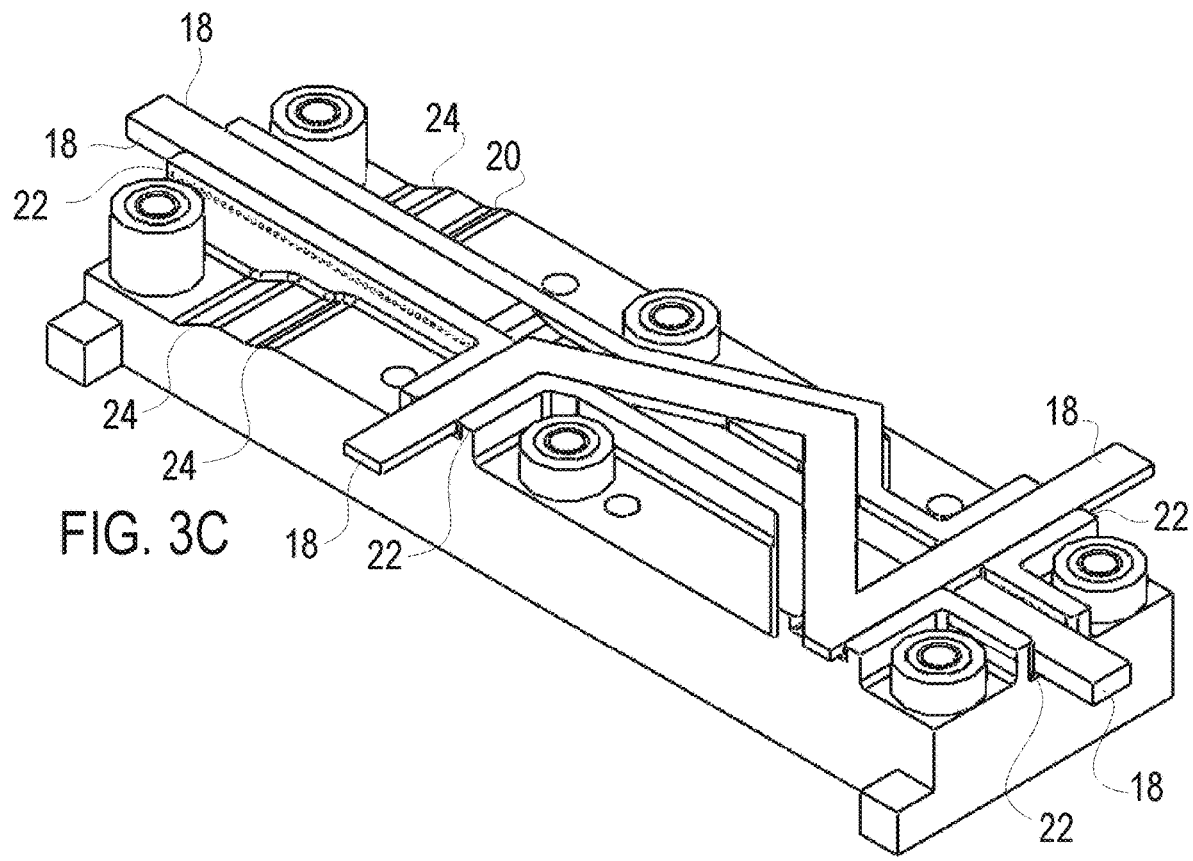
FIG. 3C is a perspective view of the fixed frame formed as a fiber crossing frame of FIGS. 3A and B with a top half of a housing removed.
Figure 3B:
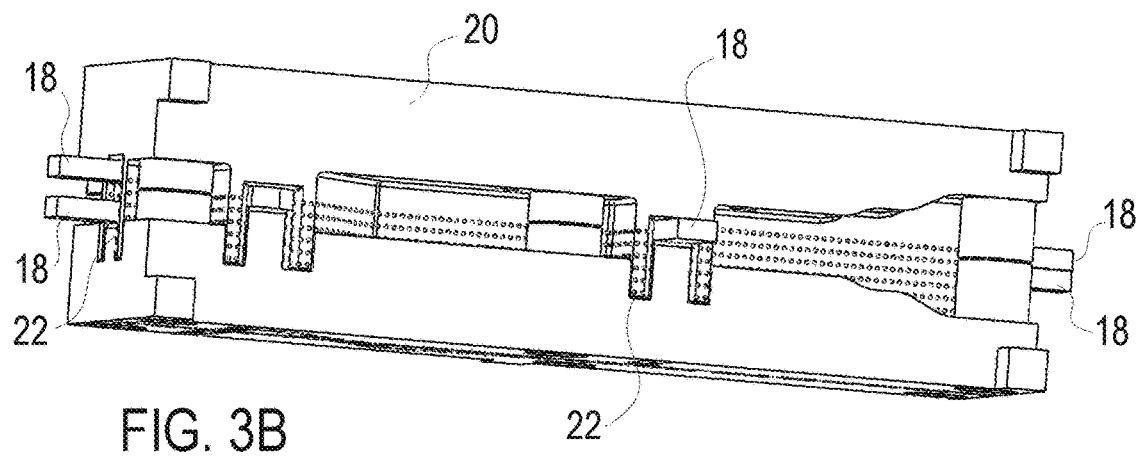
FIGS. 3A and B are perspective views of a fixed frame formed as a fiber crossing frame for use in the MRI phantom for calibrated anisotropic imaging of FIG. 2.
FIG. 3D is a perspective view of the fiber tracks within the fiber crossing frame of FIGS. 3A and B with the frame removed.

FIGS. 3A-3D illustrate a fixed frame 20 formed as a fiber crossing frame which includes at least three distinct angle fiber crossings across the fiber crossing frame 20. The fixed frame 20 of FIGS. 3A-D is formed of two halves that are bolted together to provide the desired compression on the tracks 18 extending there-through, which tracks 18 are best shown in FIG. 3D. The fiber crossing frame 20 includes a lower tract pathway 22 supporting a lower track 18 within the fixed frame 20, an upper tract pathway 22 supporting an upper track 18 within the fixed frame 20 which is substantially parallel with the lower track 18 across the fixed frame 20 and an intermediate tract pathway 22 between the upper tract pathway 22 and the lower tract pathway 22 supporting an intermediate track 18 between the upper track 18 and the lower track 18, and wherein the intermediate track 18 crosses the upper and lower tracks 18 at least at three distinct angles. Specifically, as shown the three distinct angles of the fiber crossings of the fiber crossing frame of FIGS. 3A-3D include 90 degrees, 45 degrees and 30 degrees (or 60 degrees), as shown. The fiber crossing frame construction shown is an easily produced construction as it only requires three tracks 18, rather than laying out individual crossing fasciculi 16 or interwoven fibers 12. The distinct test points for the crossing are, of course, where the intermediate track 18 crosses the parallel upper and lower tracks 18.

The fiber crossing frame shown in FIGS. 3A-3D has each of the tracks 18 formed of substantially the same fiber density (number of fibers per unit area). The fiber crossing frame shown in FIGS. 3A-3D may further vary the containment volume of fibers 12 at distinct test points via compression steps 24 to provide fiber density variations along the fiber crossing frame of fixed frame 20.

One test parameter that represents a quick evaluation of the analysis of the fiber crossing frame of fixed frame 20 of FIGS. 3A-D is an evaluation of the calculated measured directional simulated axonal volume taken along the path of the upper and lower tracks 18 (as this direction is consistent along the frame 20 for each crossing test point). The calculated measured directional simulated axonal volume taken along the path of the upper and lower tracks 18 should equate the known "axonal volume" of the upper and lower tracks 18 of the phantom 10 and this calculated amount should remain constant across the fixed frame 20 of FIGS. 3A-D. Thus the calculated axonal volume can be used to calibrate a system and validate crossing differentiation of the system.

Fiber Density Frame

FIG. 4 is a schematic representation of a phantom 10 incorporating a number of distinct fixed frames 20 wherein the upper horizontally extending fixed frame 20 is formed as a fiber density frame which includes fiber density variations across the fixed frame 20, whereby the fibers 12/unit area in the fixed frame 20 are provided at distinct known varied amounts at least at a number of distinct test points across the fixed frame 20.

The fixed frame 20 formed as a fiber density frame includes a series of ten adjacent columns, although other starting numbers are possible, defining a tract 22 pathway there-through for a track 18, with the pathway 22 interconnecting the adjacent columns. Between adjacent columns a select number of fasciculi 16, forming 10% of the original track 18 fiber number, are diverted/separated from the track 18 before the track 18 reaches the next adjacent column. This construction provides an easy way for the fiber density frame to vary the number of fibers 12 at each column to provide fiber density variations across the fixed frame 20. The fixed frame 20 here is configured to vary the number of fibers 12 by a fixed fiber amount (e.g., 10%) in adjacent columns Additionally the depth of the fixed frame 20 at each column includes steps 24 to vary the containment volume of fibers 12 along the column to provide for a distinct process of providing fiber density variations. The confinement volume ranges are shown as 1, 1.5, 2 and 3, and these are given as relative volumes relative to the size of the track 18 with no interstitial water (i.e. only fibers 12), with this relative size being 1 at the most constrained location. The remaining steps are 1.5, 2 and 3 times this volume respectively. Alternative compression steps are possible, e.g., 1.0, 1.24, 1.50, 2.0.

The fixed frame 20 formed as a fiber density frame provides 40 distinct test points, with one test point being associated with each confinement volume at each column. The MRI system can be expected to control the simulated axonal volume by fiber amount and confinement amount as well as control and provide reference measurement of the hindered volume by fiber amount and confinement amount. Graphically these test results should appear as linear points across each confinement size of each column. The fiber density frame 20 provides a calibration for a system and verification of accuracy across a range of fiber densities representing more accurate representation of the range of fiber densities that will be seen in human physiology. It may be advantageous to provide this fiber density frame 20 in various orientations to validate the system in distinct directions.

As noted above some conventional MRI fiber tracking has difficulty imaging axons much beyond two times the maximum compression volume, which is defined as the volume without interstitial or hindered water.

Hindered and Restricted Water Fixed Frames

FIG. 4 is a schematic representation of a phantom 10 incorporating a number of distinct fixed frames 20 wherein immediately below the fiber density frame 20 is a fixed frame 20 including tracks 18 in which the hollow tubular fluid 14 within the fibers 12 and the interstitial fluid between the fibers 12 is formed of both water and deuterium oxide, which operates as discussed above. FIG. 4 shows a similer set of fixed frames 20 for calculation of hindered and restricted water extending vertically (behind the fiber density frame 20) and end to end (labeled "through plane"). This orthogonal arrangement allows the system to measure hindered and restricted water along three axis. Additionally the hindered and restricted water fixed frames may be duplicated for distinct fiber densities, with only one frame being shown for clarity.

An alternative fixed frame 20 for analysis of hindered and restricted water is to form two distinct tracks 18 with similer fiber 12 paths, and densities except one track 18 has unfilled (air filled) hollow fibers 12 with sealed ends, while the other has the fibers 12 filled with fluid 14. In this arrangement the MRI results of the air filled fibers 12 will only show the interstitial water (or heavy water) signals.

Fiber Crossing Frame

FIG. 4 is a schematic representation of a phantom 10 incorporating a number of distinct fixed frames 20 wherein immediately below the horizontal hindered and restricted water fixed frame 20 is a crossing angle fixed frame 20 substantially as described above, expect this fixed frame 20 illustrates five crossings at 0 degrees, 15 degrees, 30 degrees 45 degrees and 90 degrees. The construction and operation is substantially similer to that described above and is shown to illustrate the variability of fixed frames 20. It may be advantageous to provide this fiber crossing frame 20 in various orientations to validate the system in distinct directions.

Crossing Density Frame

FIG. 4 is a schematic representation of a phantom 10 incorporating a number of distinct fixed frames 20 wherein immediately below the crossing angle fixed frame 20 is a crossing density fixed frame 20.

The crossing density frame includes four angle fiber crossings across the fixed frame 20, wherein the angle fiber crossings include a plurality of distinct fiber densities. Specifically the crossing density frame can be formed analogous to the crossing angle frame (except the crossing angle is maintained the same at 45 degrees), wherein the crossing density frame includes a lower tract pathway supporting a lower track 18 within the fixed frame 20, an upper tract pathway supporting an upper track 18 within the fixed frame which is substantially parallel with the lower track 18 extending horizontally across the fixed frame 20 as shown and a plurality of intermediate tract pathways between the upper tract pathway and the lower tract pathway each supporting an intermediate track 18 between the upper track 18 and the lower track 18. Each intermediate track crosses the upper and lower tracks 18 at the same crossing angles, respectively; however the intermediate tracks have a variety of fiber densities. In addition to the three layers tracks 18 as shown the crossing frame 20 may be formed with inter-digitizing or weaving smaller subsets of the fibers 12 for a more realistic crossing frame, however the three layer structure of the figures is sufficient for illustration of the concept. The densities shown are 5.0, 2.0, 0.5 and 0.2 and are measured relative to the upper and lower tracks 18. As with the fixed frame of FIGS. 3A-D, the calculated measured directional simulated axonal volume taken along the path of the upper and lower tracks 18 should equate the known "axonal volume" of the upper and lower tracks of the phantom 10 and this should remain constant across the fixed frame. Again the variance of crossing fiber densities represents a more realistic representation of expected physiology and the phantom 10 needs to accommodate and validate this aspect of fiber tracking. It may be advantageous to provide this crossing density frame in various orientations to validate the system in distinct directions.

Routing Frame

Figure 5:
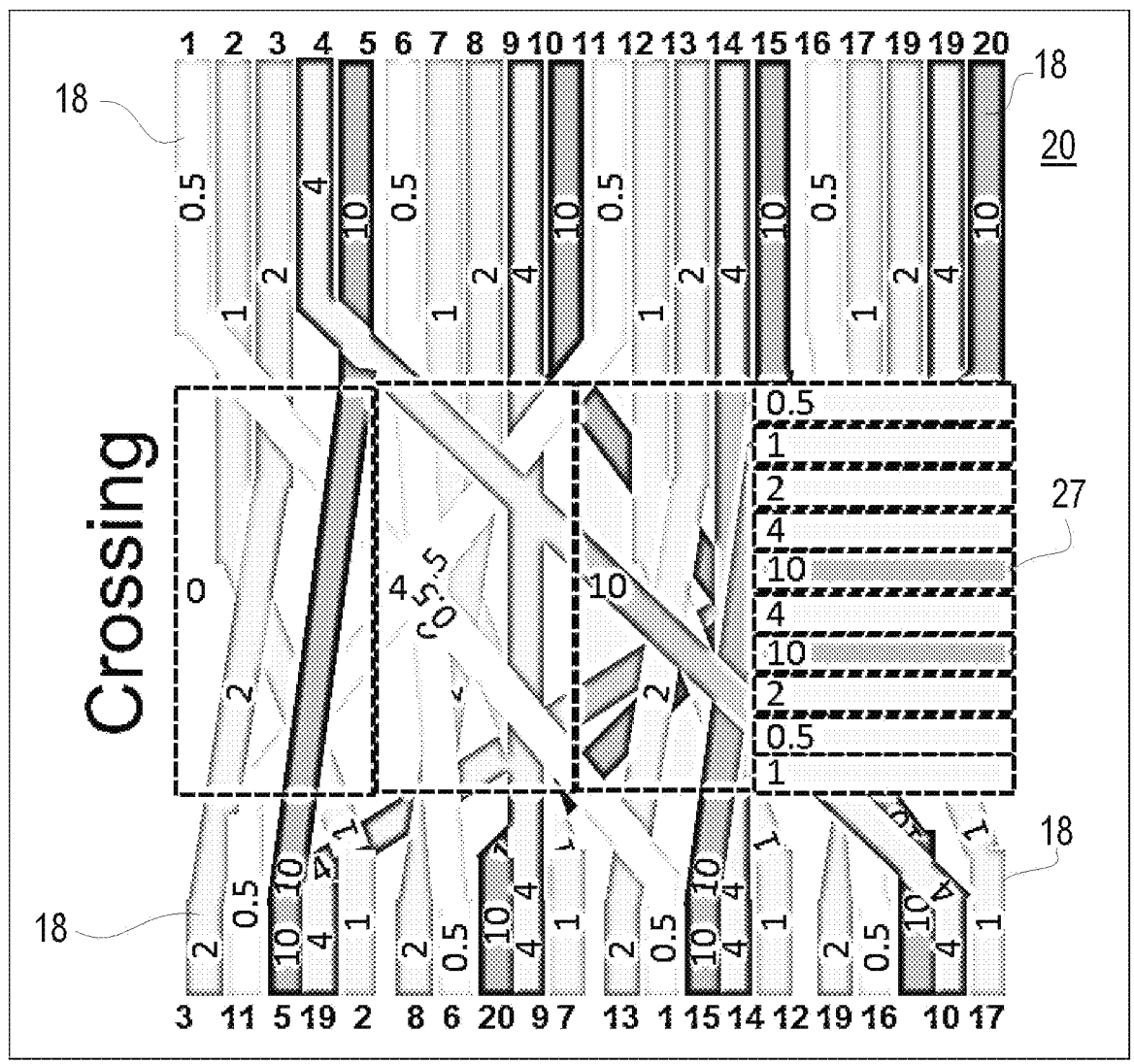
FIG. 5 is a schematic view of a routing frame for an MRI phantom for calibrated anisotropic imaging according to one embodiment of the invention.

FIG. 5 schematically illustrates a fixed frame 20 for the phantom 10 which is formed as a routing frame which includes a plurality of distinct track starting locations at one end thereof shown across the top and labeled 1-20. The routing frame 20 includes a plurality of aligned track ending locations at an opposed end thereof also labeled 1-20 in a different order from the top location. The routing frame includes tracks 18 extending from the starting locations to the ending locations of the same number, wherein substantially all of the tracks 18 end in an ending location that is not aligned with the respective track's starting location so that the tracks 18 cross each other.

The routing frame provides a validation for tracking the correct fiber path. It may be advantageous to provide this routing frame in various orientations to validate the system in distinct directions. As shown the routing phantom includes tracks of varying fiber densities, specifically a pattern of five track 18 fiber densities (i.e. the number of fibers per area) repeated four times.

The routing phantom includes extraneous tracks 27 extending directionally across the routing frame. The tracks 27 are effectively added noise, although the system could track the noise like any other fiber bundle set. As shown the routing frame further includes distinct areas of crossing fibers or tracts 27. The first area has no tracts 27, the second area (labeled 4) incorporates 4 noise tracks 27 (not shown), the third area has 10 noise tracks 27 (not shown) while the final area also has 10 noise tracks 27 and adds varying fiber densities to the noise tracks 27 as shown.

Mapping routing accuracy possibly broken down by tract density, for the routing fixed frame will be useful for validating and calibrating the system.

Physiologic Simulation Frame

Figure 6B:
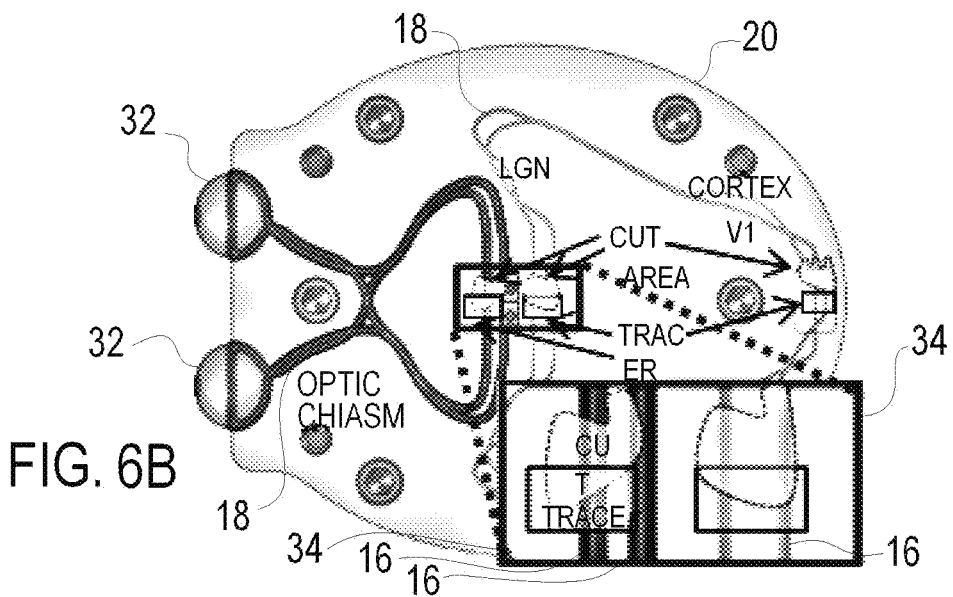
FIG. 6B is a schematic view of the physiologic simulation frame of FIG. 6A.
Figure 6A:
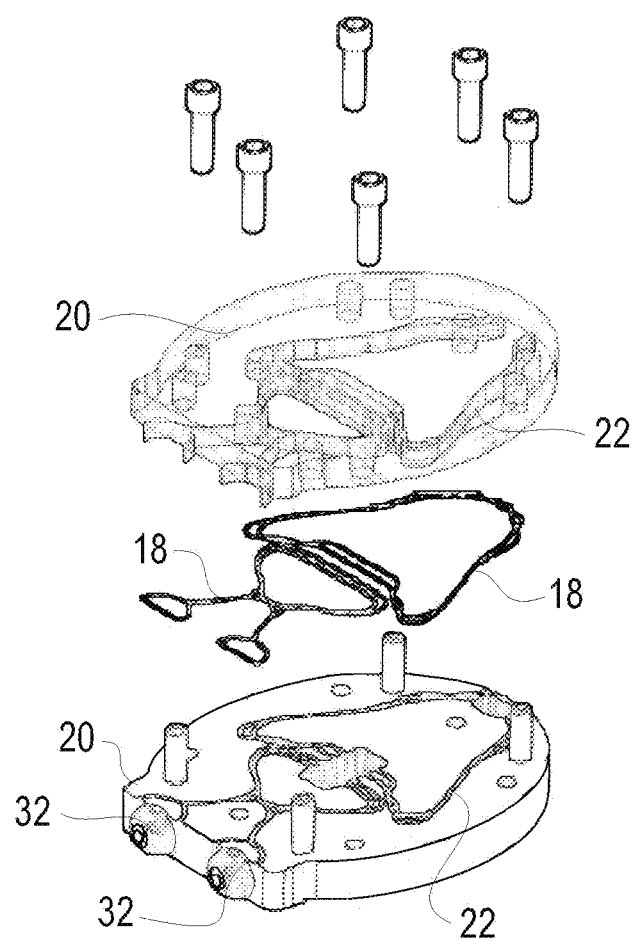
FIG. 6A is a schematic exploded view of a physiologic simulation frame for an MRI phantom for calibrated anisotropic imaging according to one embodiment of the invention.

FIGS. 6A and B schematically illustrate a fixed frame 20 for the phantom 10 which is formed as a physiologic simulation frame and includes a shell simulating a human cranium, simulated eyes 32 and tracks 18 simulating known physiologic optical neural tracts from the simulated eyes 32. The fixed frame of FIG. 6 illustrates the aspects of the fibers 12 filled with fluid 14, namely that a, simplified, realistic representation of the physiologic fiber tracts can be formed and tested. The physiologic simulation frame may be made as complex as time and money allows, however including conventional and critical fiber crossings of distinct fiber densities should be sufficient for testing. The one addition to the physiologic simulation frame of FIG. 6 which includes tracks 18 within pathways 22 for simulating known physiologic optical neural tracts from the simulated eyes 32 is the inclusion of a pair of segments 34 in which the frame spreads individual fascicule 16 to serve as an unmistakable starting point for fiber tracking.

Concurrent Phantom

It should be apparent that each fixed frame 20 described, is itself an MRI Phantom. However as noted above a plurality of fixed frames 20 could be used together to calibrate and validate distinct aspects of a system or technology and they may be placed at distinct orientations to simultaneously validate in different orientations.

Figure 7:
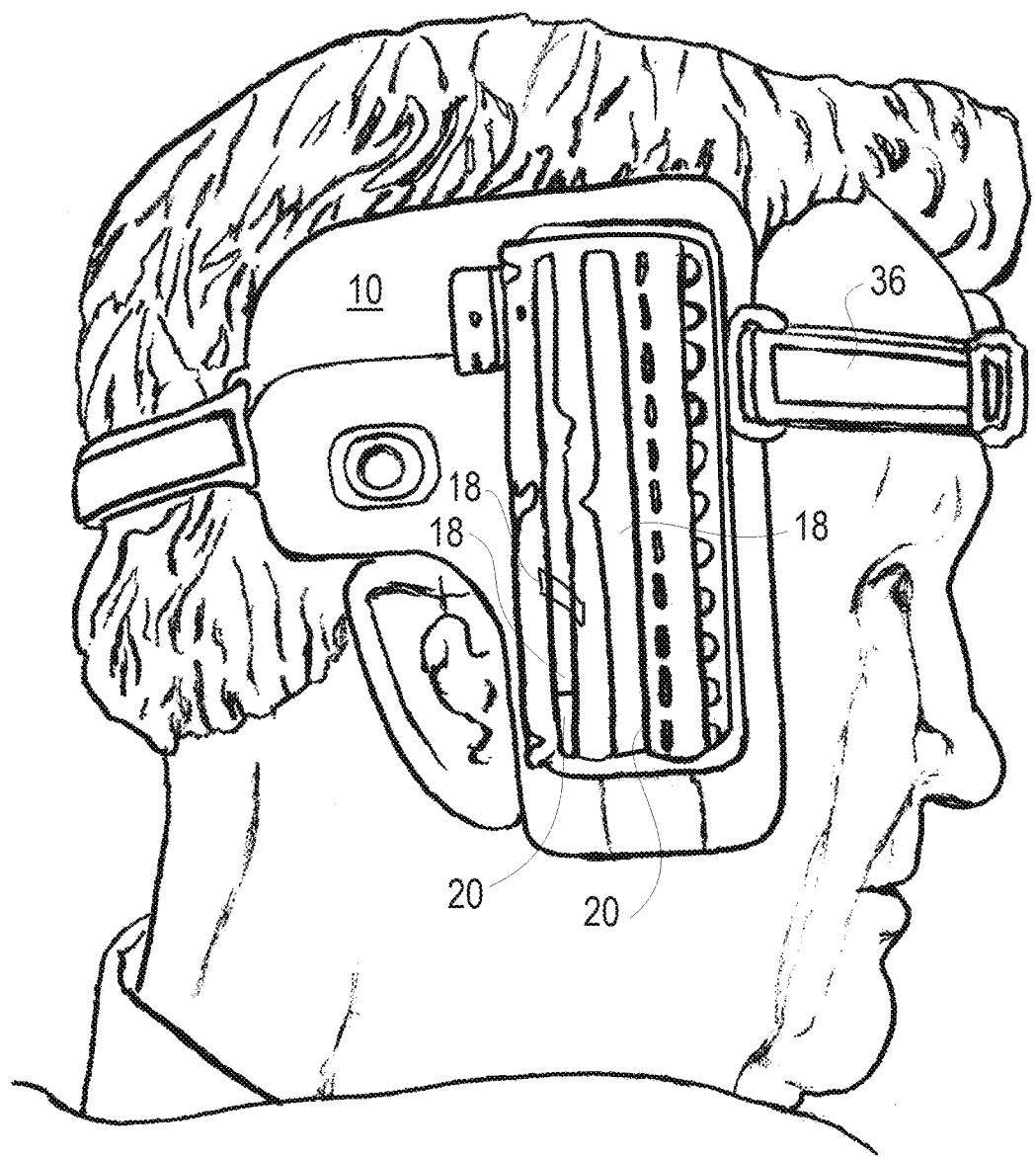
FIG. 7 is a side view of a subject worn MRI phantom for calibrated anisotropic imaging according to one embodiment of the invention.

The phantom 10 of the present invention provides a tool for validating new algorithms for fiber tracking. Separately the phantom 10 provides the basis for a periodic checking of an MRI system as part of regimented quality control for validation and calibration of the device. Further, a phantom 10 according to the present invention may be worn by a patient, referenced herein as a concurrent phantom 10, to provide a patient by patient, scan by scan, continuous validation of a machine. FIG. 7 illustrates one version of a concurrent phantom 10 according to the invention, and it includes a strap 36 to secure the phantom 10 to the user. The phantom 10 may be automatically checked by the system and alert the technician to out of alignment results, thus saving a significant number of wasted scans (typically the wasted scans would be those occurring throughout the rest of the day at over $1000/hour of running time). This phantom 10 is a small version of the full phantom, about the size of a deck of cards (13 cm×6 cm×2 cm), which could be placed over the left ear of the patient during scanning in order to measure fiber 12 content, providing a baseline for each scan session. Alternatively, it may be built into a cap worn by the patient during the scan, and would contain a fiber track 18 with controlled confinement, crossing of tracks 18, and loss of fibers 12 (via bundles 16), providing a reference to calibrate data across scans.

The concurrent phantom 10 will give value to the patient. As a hypothetical, in 2016, a patient consult could include a comment such as: "In the eight HDFT MRI scans you have had in your career, each time you wore a blue box on the left side of your head. Inside were millions of hollow textile tubes, smaller than hairs, which have the same shape and density of the axons that make up the cables in your brain. The fact that these tubes are consistent across time gives us confidence that the change we see is in your head and not due the different equipment you were scanned on. The drop to 50% on the arcuate cable after your twelfth IED explosion shows real anatomical loss of the brain cable that supports working memory. After rehabilitation therapy, your scan shows 25 percent recovery of this cable."

For the war veteran, knowing where the wound is and its extent enables seeking rehabilitation in that they appreciate that there is an anatomical brain loss. Seeing a broken bone in an X-ray helps the patient and physical rehabilitation team to design and complete targeted rehabilitation of the orthopedic injury. Similarly seeing the reduced brain tract provides the patient with resolve to exercise the brain tissue to induce growth and alternative connectivity and recover function. Seeing improvement during rehabilitation results in even greater resolve to continue working on recovery. A stable quantitative referent may be helpful to understand the trauma-induced change in the years following an injury. The ability to quantify reduction and recovery in extent of axonal diffusion will improve the understanding of the nature of brain trauma and recovery.

Kissing, Branching and Funneling Phantoms

The discussion of the fibers 12 and the construction of fixed frames 20 above will indicate that the construction of fixed frames 20 in the form of routing frames that exhibits kissing fiber tracks 18 (those that have fibers 12 or fascicules 16 that approach each other and are concurrent for a segment then diverge without crossing); branching fiber tracks 18 (fibers 12 or fascicules 16 that begin in one bundle or track 18 and separate in to different tracks 18); funneling fiber tracks 18 (Fibers 12 or fascicules 16 that begin as separated and merge to form a single track 18); and combinations of these will also be of interest for validation and calibration phantoms 10.

Conclusions Regarding Phantom 10 for Calibrated Anisotropic Imaging using Fluid 14 Filled Fibers 12

The present invention has developed a phantom 10 for calibrated anisotropic imaging using fluid 14 filled fibers 12 that will allow for phantom-calibrated quantification of axonal integrity and axonal loss for detection of diffuse axonal injury (DAI) from TBI. It is critical to be able to quantify and calibrate measurement accuracy in research and medicine. Calibrating a measurement is fundamental to longitudinal cross-instrument combination of those measurements. As of July 2015 there is no such calibration for measures of diffusion anisotropy in brain fiber tracts which exists at any DoD/VA or civilian hospital. The present phantom 10, for the first time, provide such technology for white matter tracts, which are the leading organ of Diffuse Axonal Injury (DAI) damage in both animals and man. MRI phantoms have been valued for decades for their ability to evaluate, analyze, and improve the accuracy, precision, and stability of various MRI measures. There is a critical need for phantoms specifically dedicated to diffusion imaging. Although glass and plastic capillaries and a variety of plant and synthetic fibers (e.g., hemp, linen, viscose, rayon, polyamide twine and Dyneema) have been used with varying success to approximate diffusion properties of the human brain, none have been adequately developed for large-scale use in laboratory and clinical research applications. The present phantom 10 overcomes these deficiencies.

Figure 10A:
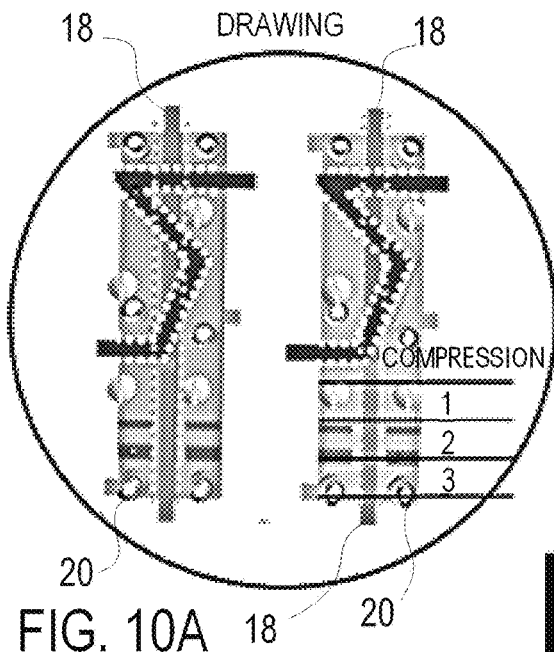
FIGS. 10A-C illustrates an MRI phantom for calibrated anisotropic imaging according to the invention and representative scans of the MRI phantom.
Figure 10B:
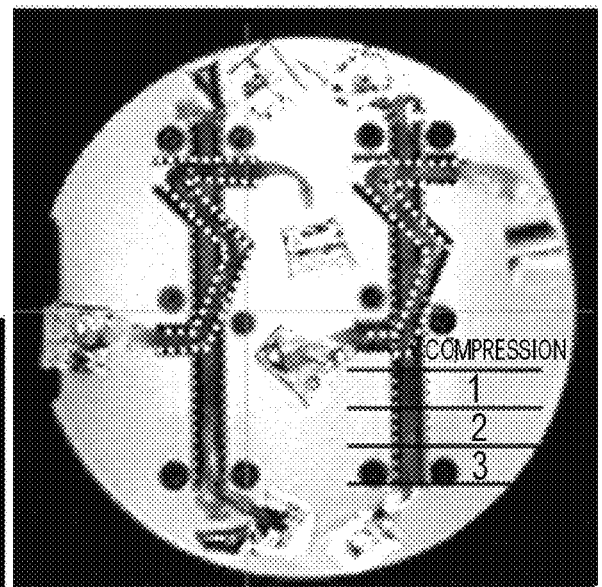
Figure 10C:
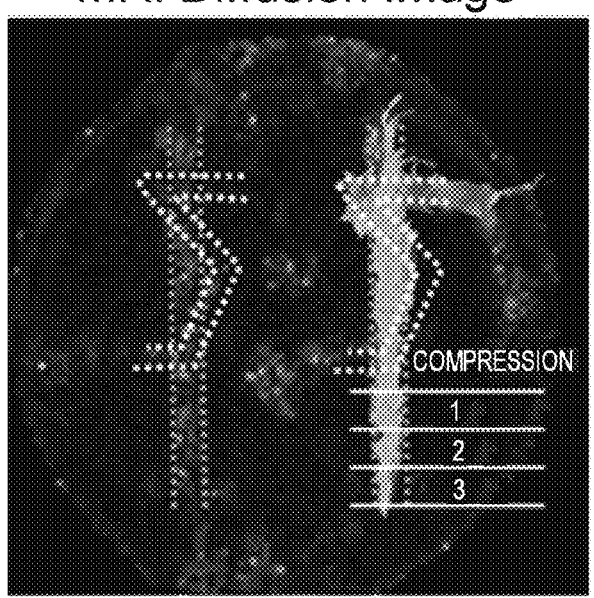

FIGS. 10A-C illustrates representative scans of an MRI phantom 10 for calibrated anisotropic imaging according to the invention. FIG. 10A illustrates a phantom 10 with a pair of adjacent crossing frames as discussed above in connection with FIGS. 3A-D. Here one of the frames is formed with fibers that were left unfilled while the other is filled with water for illustration purposes. FIG. 10B is an illustration of an MRI T1 structural image of the phantom 10 of FIG. 10A, and the lack of fiber tracking/fiber illustration is noticed. FIG. 10B is an illustration of an MRI Diffusion image of the phantom 10 of FIG. 10A. The ability of this particular system and algorithm to correctly map crossing fibers can now be quantified and calibrated. Additionally of note is the ability to track fibers at distinct densities. The distinction of the MRI diffusion image of fibers at 1, 2 and 3× maximum constriction volumes is observable. FIGS. 10A-C demonstrates some of the applications of the phantoms 10 of the present invention.

This phantom 10 is designed to replicate the complex pattern of crossing white matter fibers in the human brain, and will provide ground truth for measurements of compartmentalized water in axons. The phantom 10 described herein provides precise and repeatedly manufactured axonal diffusion structures to separate and quantify intra-axonal water (termed restricted in the MRI literature) and extra-axonal water (the water between the axons termed hindered water), and free water or isotropic diffusion. The phantom 10 is composed of hollow fiber, micron-scale textiles manufactured and arranged at controlled crossing and packing densities in two and three dimensions. The phantom 10 provides ground truth quantification of axonal tract structures, as well as to quantify accuracy and interpretability of diffusion measurements across vendors, instruments, acquisition, and analysis procedures.

The fibers 12 can be precisely manufactured with controlled packing densities, crossing angles, and curved trajectories, replicating axonal tracts with sub-millimeter precision and micron-level control of axonal diameters. An axon is a tube, 0.5-20 microns in diameter, which may be of long length (a 10 cm axon may have a length-to-diameter ratio of 10,000 to 1). This length-to-diameter ratio is the defining property of the directional axonal imaging that is the basis of diffusion tensor imaging and subsequent technologies. The phantom provides a "ground truth" value for variables used to model diffusion in dMRI, with direct relationship to physiologic anatomy (e.g., tube diameter, tract shape, and interstitial space and fluids). The phantom 10 allows for quantification measurement error in the pipeline. The textiles are stable, such that they can be disassembled from the phantom 10 and re-measured to verify maintenance of the water content over years of storage and use.

The phantom 10 provides a calibration standard across sites, as well as a ground truth structure to advance tract diffusion analysis. The phantom 10, in operation, will determine the ability of specific MRI diffusion acquisition parameters (angles and b-values) to quantify known fiber 12 loss of fibers. The development of the phantom 10 provides the field with the first ever axon-scale, hindered-water, fiber-crossing phantom 10, which will deliver ground truth measurement of compartmentalized diffusion. Although there have been several glass and fiber-oriented diffusion phantoms, none have been able to emulate the hindered water (water in axonal scale tubes) and crossing angles of real brain fibers.

The ground truth simulation reference of phantom 10 will for the first time provide the field, and DoD imaging centers, with a calibration tool for the measurement of axonal loss, which can be used to improve the quality of fiber tracking data in the research community and hospitals. It will provide the key technology for career-long measurement of military personnel of tract integrity across sites, instruments, and time, which is pivotal to providing standardization and quality control. This aim will enable future DoD/VA requirements specifications for MRI scanner acquisition to include objective specifications that an instrument be able to detect a given percentage of diffuse axonal injury. It will help provide a meaningful, calibrated measurement of TBI-induced brain damage to both the TBI wounded and the clinician teams that treat their wounds.

Universal, Modular Temperature Controlled MRI Phantom for Calibrated Anisotropic and Isotropic Imaging Following the above descriptions of the MRI phantom 10 for calibration and validation for anisotropic imaging discussed in connection with FIGS. 2-7 and 10A, the universal, modular, temperature controlled MRI phantom 10 for calibration and validation for anisotropic and isotropic imaging is shown in FIGS. 11A-E and comprises an outer insulating shell 200 configured to be received within an MRI chamber (shown in FIG. 11B); an inner shell 210 is received within the outer insulating shell 200; Fluid conduits 220 formed in a base 222 adjacent the inner shell 210 for receiving temperature controlling fluid or gas cycling there-through; and a series of stacked layers 230 of frames 20 containing test points for the MRI phantom, including at least some anisotropic imaging test points in at least one frame 20 and at least one isotropic imaging test point in at least one frame 20.

Outer Insulating Shell 200

The outer insulating shell 200 is preferably a foam insulating layer such as Styrofoam or expanded low density Polyethylene (eLDPE) or similar insulating foams which are MRI compatible. The insulating shell 200 serves two functions. The first is insulation to assist in maintaining the temperature of the MRI phantom 10 substantially constant (i.e. +/−8 degrees, although preferably +/−4 degrees, and most preferably +/−2 degrees) throughout a typical calibration testing. The insulation 200 together with the temperature control elements allow the phantom 10 of FIGS. 11A-E to be operated at other than ambient temperatures (freezing, human body, or other desired temperature) and to be operated at consistent temperatures (+/−8 degrees, and preferably +/−4 degrees and most preferably +/−2 degrees) to prevent a thermal drift in the resulting signals. The phantom 10 can be operated at any desired temperature, however a fixed temperature around 60-70 degrees F. may be most efficient as this temperature can utilize forced air cooling available in the MRI environment to maintain the desired temperature in use. Maintaining the phantom 10 at human temperature (98.6 degrees F.) or at freezing (32 degrees F.) is possible and has been proposed for other MRI operations. The Phantom 10 is designed to provide this utility. The preferred implementation is at body temperature.

Figure 11A:
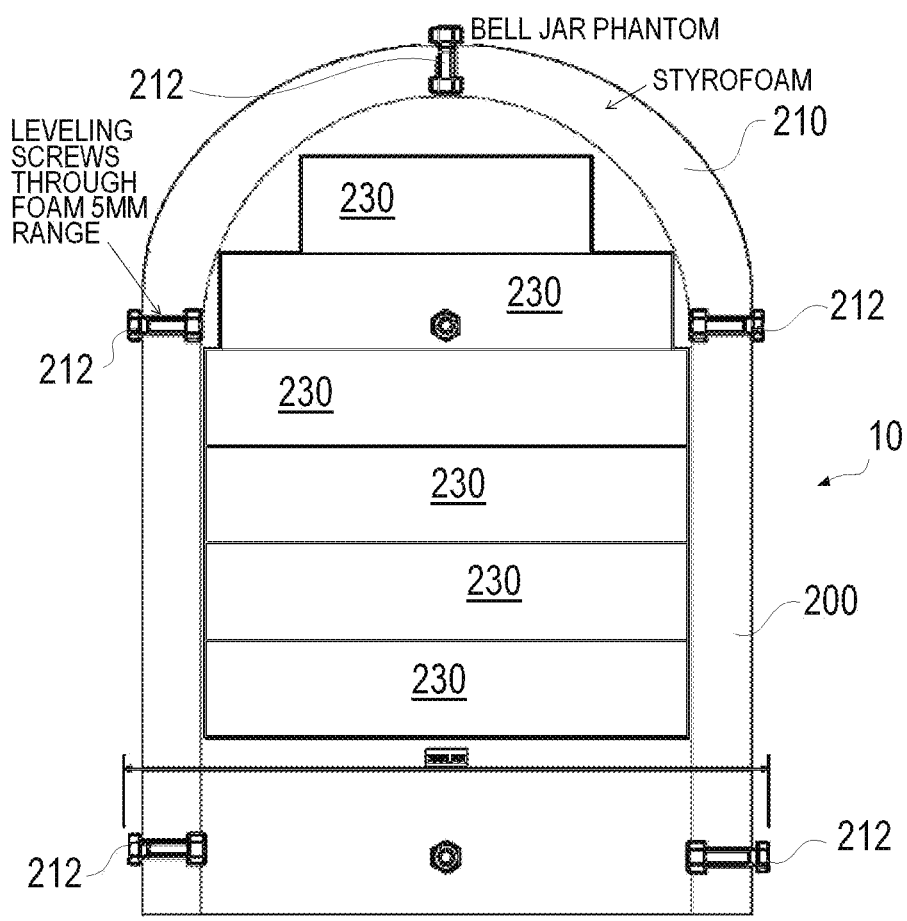
FIG. 11A is a schematic sectional view of a universal, modular, temperature controlled MRI phantom for calibrated anisotropic and isotropic imaging according to the invention.
Figure 11B:
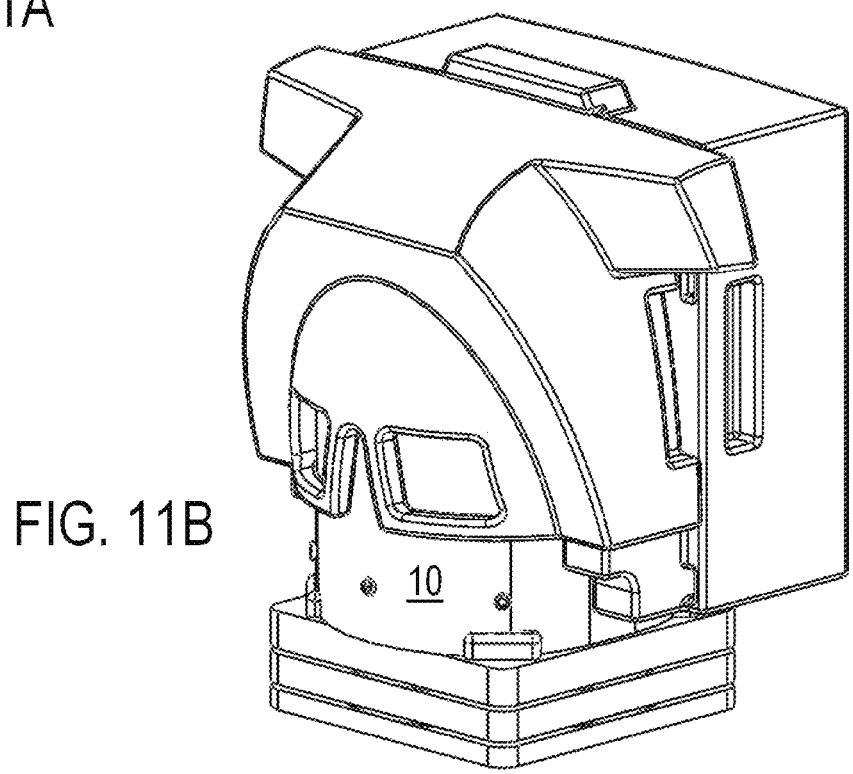
FIG. 11B is a perspective view of the universal, modular, temperature controlled MRI phantom of FIG. 11A within a head coil.

Aside from its insulating properties the outer insulating shell 200 serves the function of fitting the phantom 200 to the specific MRI coil environment. The outer shell 200 can be formed specific to a given make and model of MRI, with the remaining elements of the MRI phantom 10 being consistent across all models. With this specific shell 200 the operators can easily place the phantom 10 in a precise location within the coil as will be fixed by the specific outer shell 200, as generally shown in FIG. 11B. Assisting in this fitting function the outer shell 200 includes leveling screws 212 fixed to inner support frame 214 upon which the foam of shell 200 is mounted. This structure will also assist in operation as the placement step becomes simple and easily and consistently accomplished by technicians with minimal effort. The shell 200 will precisely fit the MRI phantom 10 in the associated head coil. The phantom 10 remains universal as the outer shell 200 is easily formed for each specific head coil shape. The head coil shown in FIG. 11B is a Siemens 32CH™ brand head coil and represents the smallest head coil space on the market assuring that the phantom 10 will be easily accommodated in all commercial MRI systems.

Simulated Fat Layer 206

The phantom 10 includes a simulated fat layer 206 surrounding the inner shell 210 to simulate the layer of fat or dermal layer surrounding the human head. The fat layer 206 can be formed as a channel or space filled with oil, such as tree nut oil, to effectively simulate the desired layer. Other materials such as a plastic mesh layer, or other material layer, can be used if it provides the correct MRI signal. The layer 206 provides added reality to the measured MRI results.

Inner Shell 210

Figure 11C:
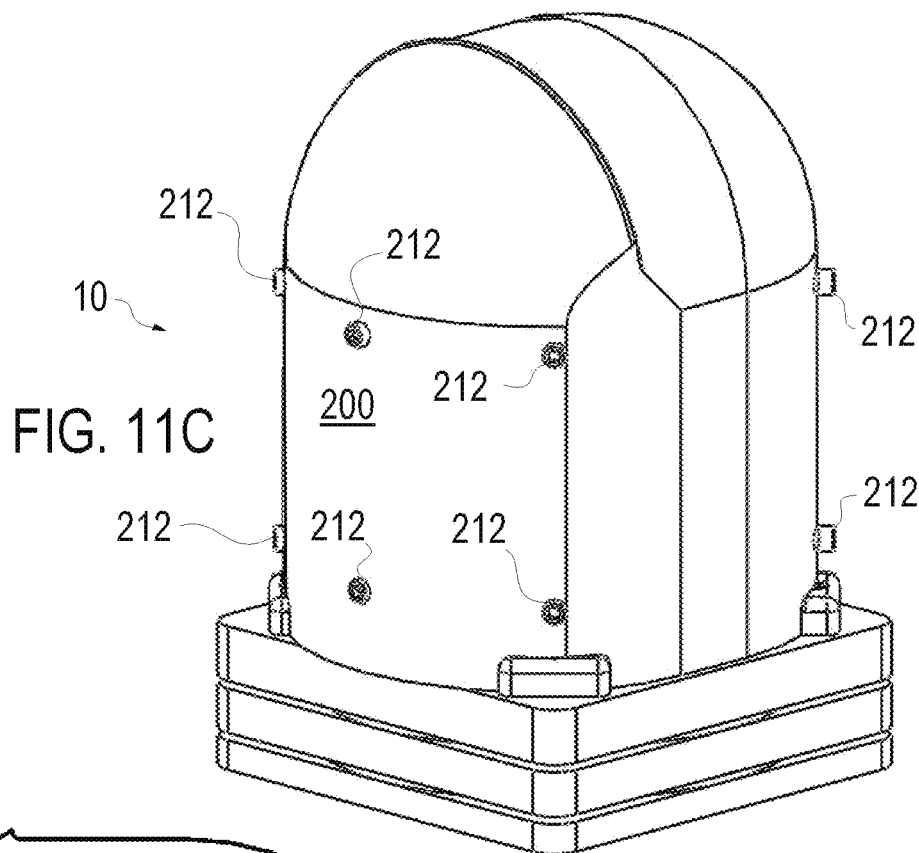
FIG. 11C is a perspective view of the universal, modular, temperature controlled MRI phantom of FIG. 11B with the head coil removed for clarity.
Figure 11D:
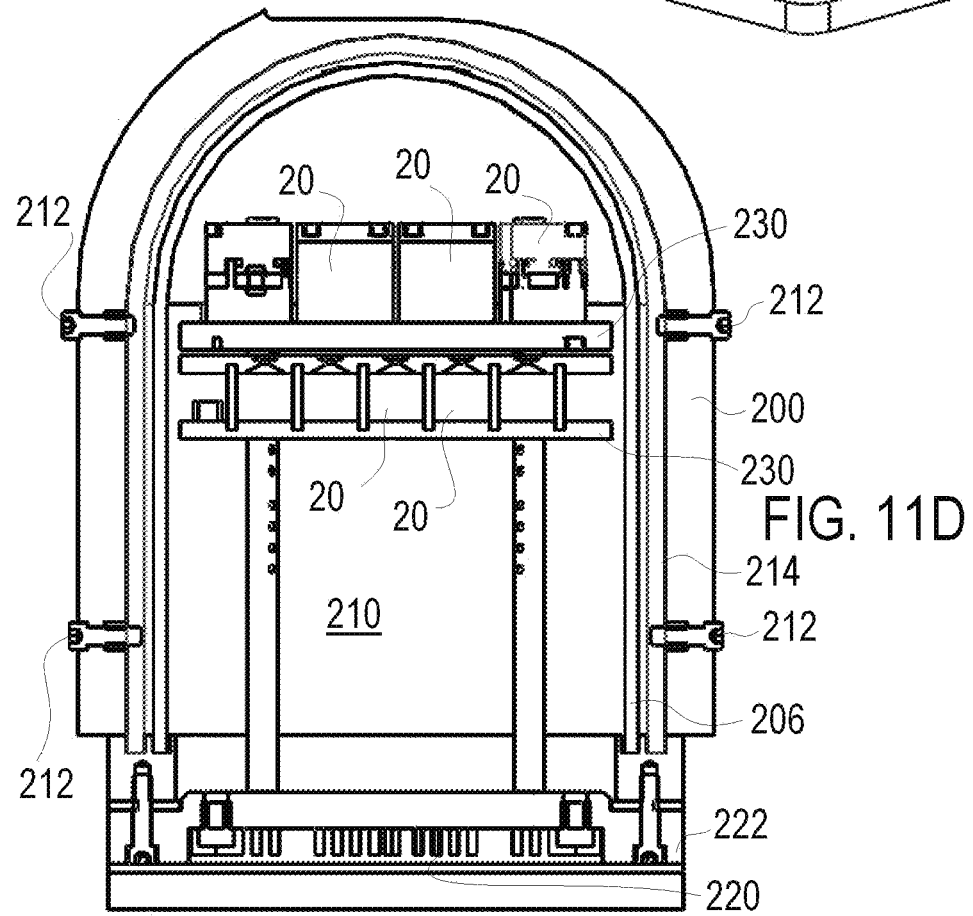
FIG. 11D is a sectional view of the universal, modular, temperature controlled MRI phantom of FIG. 11B with the head coil removed for clarity.
Figure 11E:
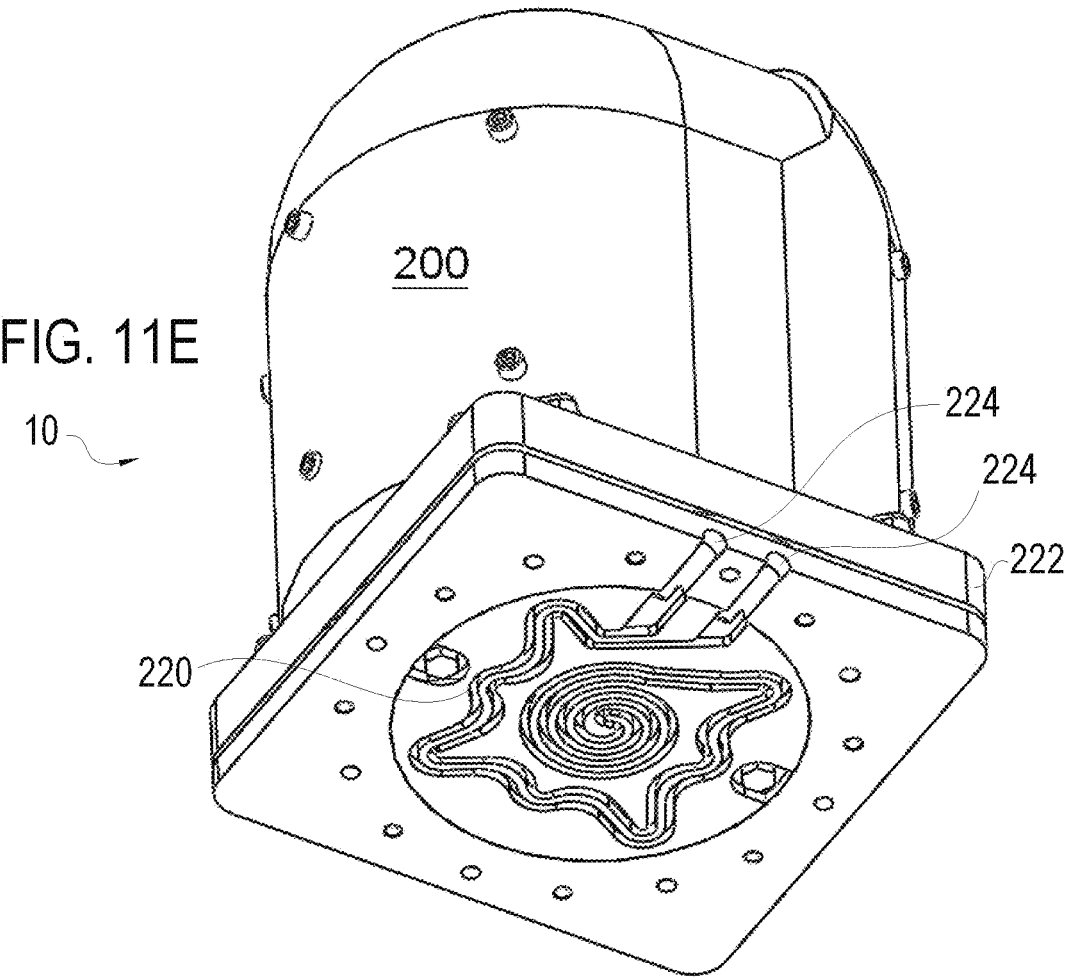
FIG. 11E is a bottom cross-sectional view of the universal, modular, temperature controlled MRI phantom of FIG. 11B.

The inner shell 210 houses the individual testing points of the phantom 12 within a series of stacked layers 230 of frames 20. The inner shell 210 may preferably be filled with fluid, generally water or possibly heavy water. The frames 20 can be of any known phantom or frame design including those as detailed above for anisotropic imaging test points. The frames 20 may be chambers, or include chambers, such as the isotropic test points of the frames in FIG. 13 or possibly where the frame 20 has fibers 18 with intersticial fluid differing from the fluid within inner shell 210. The universal phantom 10 preferably includes at least some anisotropic imaging test points (shown in FIG. 11C in the upper layer 230) in at least one frame 20 and at least one isotropic imaging test point in at least one frame 20 (shown in the lower layer 230 in FIG. 11C, as detailed below). Only two layers 230 are shown in FIG. 11C for clarity but as schematically illustrated in FIG. 11A several more layers can be accommodated within the phantom 10 as desired.

Temperature Control

As noted above the temperature control elements together with the insulation 200 allow the phantom 10 of FIGS. 11A-E to be operated at other than ambient temperatures (freezing, human body, or other desired temperature) and to be operated at consistent temperatures (+/−8 degrees, and preferably +/−4 degrees and most preferably +/−2 degrees) to prevent a thermal drift in the resulting signals. The temperature control elements comprise fluid conduits 220 formed in a base 222 adjacent the inner shell 210 for receiving temperature controlling fluid or gas cycling there-through. Ports 224 in base 222 allow the fluid conduits 220 to be coupled to a source of heating or cooling fluid or gas. When the phantom 10 is not in operation it can be coupled to a separate source of temperature controlling fluid or gas (i.e., a heater and pump—not shown) which is part of a temperature maintaining docking or storage station. In operation the insulation 200 can maintain the phantom substantially at a constant temperature throughout the calibration step in the MRI. It is possible that within the MRI environment the ports 224 can be coupled to the forced air source commonly found in such environments if the air from the source is closer to the desired constant temperature of the phantom than ambient temperatures. Further, active heating of the fluid during scanning is an alternative where the heating unit/pump exists in the MR scanning room, fluid transferred through tubes that run through an MR Scanner room waveguide, and connect directly to the phantom 10 in the scanner through couplers in the base 222. This heating apparatus can also exist in the MR Scanner room itself so long as the mechanics are kept out of the high gauss fields are contained within a Faraday cage (similar in concept to the tech used in our MRI video patent).

Additionally the temperature control may further include channels extending up into the inner shell 210 (or around the shell 210) of the phantom 10. Temperature controlling water or air (or other liquid or gas) channels could be extended into sub-channels introduced into the shell itself and/or other structures such as through layer 230 elements such as through the supporting posts 232 of the layers 230 in order to aid in heat transfer and stability of temperature. The use of effective insulation in outer shell 200 minimizes the need for additional channels in the inner shell 210

Stacked Layers 230

Figure 12A:
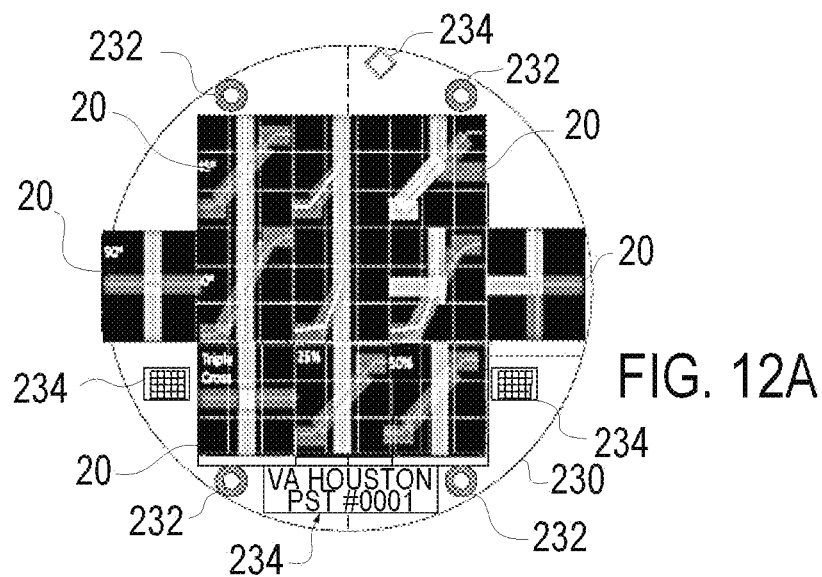
FIG. 12A is a schematic view of a crossing frame layer for anisotropic test points for the universal, modular, temperature controlled MRI phantom of FIG. 11B.

FIG. 12 schematically illustrates an anisotropic imaging layer 230 formed as a series of crossing frames 20 the details of which are generally discussed above. The layer 230 includes stacking elements or posts 232 to facilitate the stacking and mounting of layers 230. Layer 230 includes fiducials 234 to convey at least the location and orientation of the layer 230 to the MRI. Fiducial elements 234 are any marker that is visible to the MRI that can be used to register the layer 230. It is noted that the outer layer 200 with leveling screws 212 minimize the need for registration fiducials 234 as the layers 230 will be consistently placed with each testing. The fiducials 234 may be a geometric shape as shown on the top, or a readable label as shown at the bottom which can convey both information regarding where the layer 230 is (i.e. registration information) and specifically of what the layer 230 consists (information for the MRI analysis). Fiducials 234 on the two sides of the layer 230 represent a coded fiducial to convey information (more than registration information) wherein each square (or cube) of this fiducial 234 is covered with a material of a known MRI signal such that the collection of these forms an MRI compatible coded information package, like an MRI compatible bar code. In this manner the fiducials 234 can signal both position and substance to the MRI system. The fiducials 234 for the layer 230 can also be formed as the sides or edges of other structures such as posts 232 and frames 20.

Figure 12B:
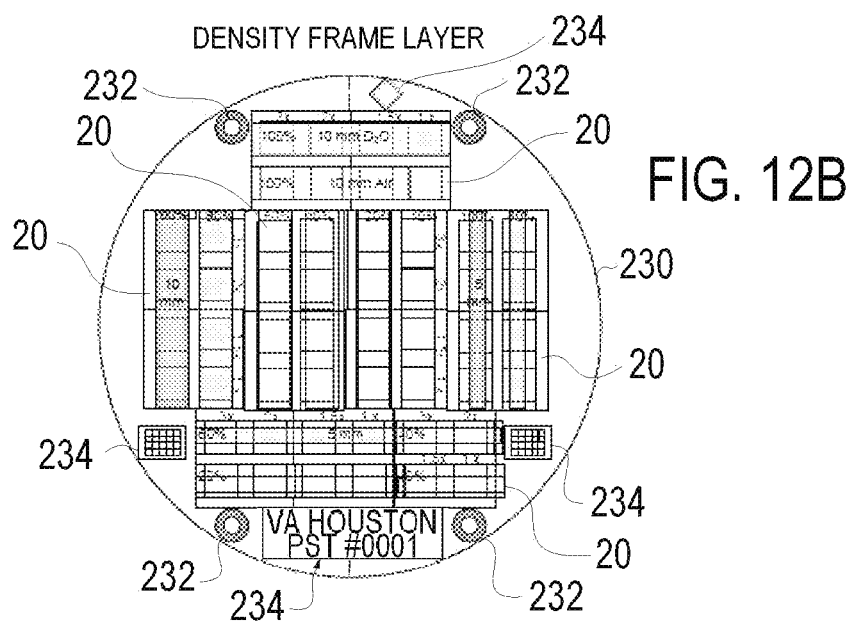
FIG. 12B is a schematic view of a density frame layer for anisotropic test points for the universal, modular, temperature controlled MRI phantom of FIG. 11B.

FIG. 12B schematically illustrates an anisotropic imaging layer 230 formed as a series of density frames 20 the details of which are generally discussed above. The layer 230 includes posts 232 to facilitate the stacking and mounting as well as fiducials 234 to convey at least the registration information for the layer 230 to the MRI as discussed above.

Figure 12C:
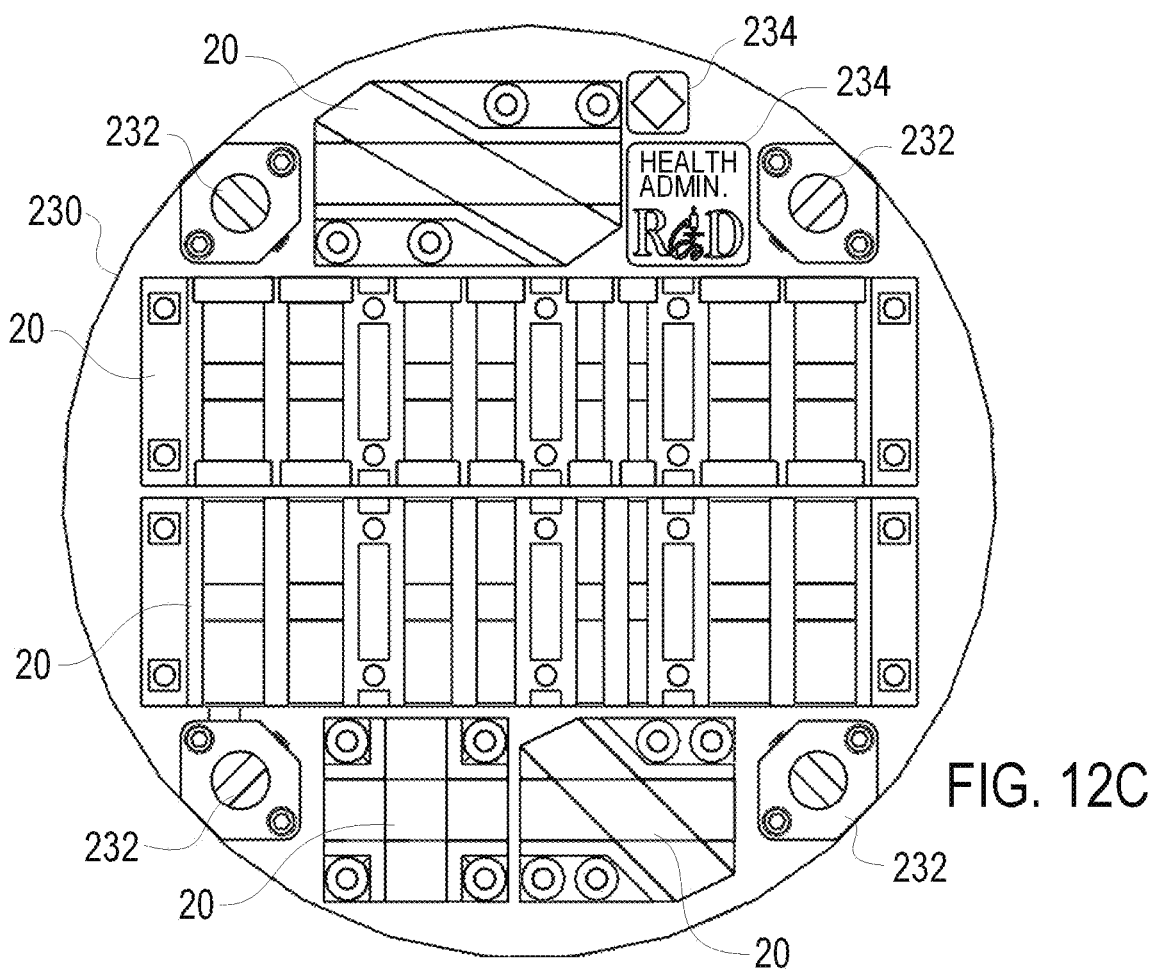
FIG. 12C is a top plan view of a frame layer for anisotropic test points for the universal, modular, temperature controlled MRI phantom of FIG. 11B with the top of the frames removed for illustration.

FIG. 12C is a top plan view of an anisotropic imaging layer 230 formed as a series of crossing and density frames 20 the details of which are generally discussed above. The layer 230 includes posts 232 to facilitate the stacking and mounting as well as fiducials 234 to convey at least the location of the layer 230 to the MRI as discussed above. FIG. 12D is a perspective view of an anisotropic imaging layer 230 of FIG. 12C.

FIG. 13 is a sectional perspective view of a frame layer 230 for isotropic test points for the universal, modular, temperature controlled MRI phantom 10 of FIG. 11B. The layer 230 is formed as an array of frames 20 in the form of rectangular chambers that are configured to receive liquids, gels or the like of known and different MRI signatures. The use of an array of distinct MRI signal materials is a known isotropic test phantom. The layer 230 of FIG. 13 further includes a conical top 240 with sealing member 242. The conical top 240 to the rectangular test point chamber allows the chamber to be filled with minimal air spaces that could interfere with the testing and any residual minimal air bubble is hopefully located out of the test area. The sealing member 242 can also serve as a fiducial and can be encoded to further convey what is in the associated chamber or frame 20. FIG. 13 also illustrates another common feature of the phantom 10 which is that the test areas are preferably rectangular as opposed to spherical as used extensively in the prior art. The rectangular test area is believed to better associate with the voxel.

It is apparent that many variations to the present invention may be made without departing from the spirit and scope of the invention. The present invention is defined by the appended claims and equivalents thereto.

What is claimed is:

1. An MRI phantom for calibrated anisotropic imaging comprising:
   hollow tubular textile fibers, wherein each hollow tubular fiber has an outer diameter of less than 30 microns and an inner diameter of less than 15 microns, and wherein at least 70 percent of the hollow tubular fibers are filled with a fluid,
   fasciculi formed by at least some of the hollow tubular fluid filled textile fibers;
   tracks formed by the combination of at least some fasciculi; and
   fixed frames supporting the tracks within the phantom, wherein at least one fixed frame is formed as a fiber density frame which includes fiber density variations across the fixed frame, whereby the fibers/unit area in the fixed frame are provided at distinct known distinct test points across the fixed frame, and wherein at least one fiber density frame will vary the number of fibers at least at three distinct test points to provide the fiber density variations, and wherein at least one fiber density frame which varies the number of fibers at least at three distinct test points to provide the fiber density variations is configured to vary the number of fibers by a fixed fiber amount in adjacent test points.

2. The MRI phantom for calibrated anisotropic imaging according to claim 1 wherein at least some fasciculi include interstitial fluid, wherein hollow tubular fluid and the interstitial fluid is formed of both water and deuterium oxide, and wherein in at least some fasciculi the hollow tubular fluid is one of water and deuterium oxide and the interstitial fluid is formed of the other of water and deuterium oxide.

3. An MRI phantom for calibrated anisotropic imaging comprising:
   hollow tubular textile fibers, wherein each hollow tubular fiber has an outer diameter of less than 30 microns and an inner diameter of less than 15 microns, and wherein at least 70 percent of the hollow tubular fibers are filled with a fluid,
   fasciculi formed by at least some of the hollow tubular fluid filled textile fibers;
   tracks formed by the combination of at least some fasciculi; and fixed frames supporting the tracks within the phantom, wherein at least one fixed frame is formed as a fiber crossing frame which includes test points for at least three distinct angle fiber crossings across the fiber crossing frame.

4. The MRI phantom for calibrated anisotropic imaging according to claim 3 wherein at least one fiber crossing frame includes a lower tract pathway supporting a lower track within the fixed frame, an upper tract pathway supporting an upper track within the fixed frame which is substantially parallel with the lower track pathway across the fixed frame and an intermediate tract pathway between the upper tract pathway and the lower tract pathway supporting an intermediate track between the upper track and the lower track, and wherein the intermediate track crosses the upper and lower tracks at least at three distinct angles, wherein the three distinct angles of the fiber crossings of the fiber crossing frame include 90 degrees, 45 degrees and 30 degrees.

5. An MRI phantom for calibrated anisotropic imaging comprising:
   hollow tubular textile fibers, wherein each hollow tubular fiber has an outer diameter of less than 30 microns and an inner diameter of less than 15 microns, and wherein at least 70 percent of the hollow tubular fibers are filled with a fluid,
   fasciculi formed by at least some of the hollow tubular fluid filled textile fibers;
   tracks formed by the combination of at least some fasciculi; and
   fixed frames supporting the tracks within the phantom, wherein at least one fixed frame is formed as a physiologic simulation frame and includes a shell simulating a human cranium, simulated eyes and tracks simulating known physiologic optical neural tracts from the simulated eyes.

6. The MRI phantom for calibrated anisotropic imaging according to claim 5 wherein in the physiologic simulation frame the tracks simulating known physiologic optical neural tracts from the simulated eyes includes at least one segment that spreads individual fasciculi.

7. An MRI phantom for calibrated anisotropic imaging comprising:
   hollow tubular textile fibers, wherein each hollow tubular fiber has an outer diameter of less than 30 microns and an inner diameter of less than 15 microns, and wherein at least 70 percent of the hollow tubular fibers are filled with a fluid,
   fasciculi formed by at least some of the hollow tubular fluid filled textile fibers;
   tracks formed by the combination of at least some fasciculi; and
   fixed frames supporting the tracks within the phantom, wherein at least one fixed frame is formed as a routing frame which includes a plurality of distinct track starting locations at one end thereof and a plurality of aligned track ending locations at an opposed end thereof and tracks extending from the starting locations to the ending locations, wherein some of the tracks end in an ending location that is not aligned with the respective track's starting location.

8. The MRI phantom for calibrated anisotropic imaging according to claim 7 wherein at least one routing frame includes tracks of varying fiber densities, and wherein more than ½ of the tracks end in an ending location that is not aligned with the respective track's starting location.

9. The MRI phantom for calibrated anisotropic imaging according to claim 8 wherein at least one routing frame further includes areas of crossing fibers which are distinct from the tracks extending to the opposed ends of the routing frame, and which are areas of distinct crossing fiber complexity.

10. An MRI phantom for calibrated anisotropic imaging comprising:
    hollow tubular textile fibers, wherein each hollow tubular fiber has an outer diameter of less than 30 microns and an inner diameter of less than 15 microns, and wherein at least 70 percent of the hollow tubular fibers are filled with a fluid,
    fasciculi formed by at least some of the hollow tubular fluid filled textile fibers;
    tracks formed by the combination of at least some fasciculi; and
    fixed frames supporting the tracks within the phantom, wherein the phantom is configured to be worn by a patient in the MRI.

11. An MRI phantom for calibrated anisotropic imaging comprising:
    A plurality of fixed frames within the phantom, each fixed frame supporting tracks which include a plurality of hollow tubular textile fibers, wherein each hollow tubular fiber has an outer diameter of less than 25 microns and an inner diameter of less than 5 microns, and wherein at least 70 percent of the hollow tubular fibers are filled with a fluid, and wherein at least one fixed frame is formed as a fiber crossing frame which includes test points for at least three distinct angle fiber crossings across the fiber crossing frame.

* * * * *